US010240203B2

(12) United States Patent
Schmidt et al.

(10) Patent No.: US 10,240,203 B2
(45) Date of Patent: Mar. 26, 2019

(54) MIRNA 320A AS BIOMARKER FOR INFLAMMATORY BOWEL DISEASE

(71) Applicant: Westfaelische Wilhelms-Universitaet Muenster, Muenster (DE)

(72) Inventors: Alexander Schmidt, Havixbeck (DE); Christoph Cichon, Everswinkel (DE)

(73) Assignee: Westfaelische Wilhelms-Universitaet Muenster, Muenster (DE)

( * ) Notice: Subject to any disclaimer, the term of this patent is extended or adjusted under 35 U.S.C. 154(b) by 0 days.

(21) Appl. No.: 15/324,032

(22) PCT Filed: Jul. 16, 2015

(86) PCT No.: PCT/EP2015/066248
§ 371 (c)(1),
(2) Date: Jan. 5, 2017

(87) PCT Pub. No.: WO2016/008971
PCT Pub. Date: Jan. 21, 2016

(65) Prior Publication Data
US 2017/0191130 A1 Jul. 6, 2017

(30) Foreign Application Priority Data

Jul. 16, 2014 (LU) .......................................... 92499

(51) Int. Cl.
*C12Q 1/6883* (2018.01)
(52) U.S. Cl.
CPC ...... *C12Q 1/6883* (2013.01); *C12Q 2600/112* (2013.01); *C12Q 2600/158* (2013.01); *C12Q 2600/178* (2013.01)
(58) Field of Classification Search
CPC ................ C12Q 1/6883; C12N 15/111; C12N 2310/141
See application file for complete search history.

(56) References Cited

U.S. PATENT DOCUMENTS

| 4,458,066 A | 7/1984 | Caruthers et al. |
| 6,770,291 B2 | 8/2004 | Smyth-Templeton et al. |
| 2011/0117111 A1 | 5/2011 | Kwon et al. |
| 2013/0143764 A1 | 6/2013 | Ogier-Denis et al. |
| 2016/0002730 A1* | 1/2016 | Ogier-Denis ........ C12Q 1/6883 435/6.11 |

FOREIGN PATENT DOCUMENTS

| WO | WO-2006/137941 A2 | 12/2006 |
| WO | WO-2009/120877 A2 | 10/2009 |
| WO | WO-2010/034479 A1 | 4/2010 |

OTHER PUBLICATIONS

Arya et al., Basic principles of real-time quantitative PCR. *Exp. Rev. Molec. Diagn.* 5(2): 209-19 (2005).
Barahona-Garrido et al., Serological markers in inflammatory bowel disease: A review of their clinical utility. *Rev._Gastroenterol. Mex.* 74(3): 230-7 (2009).
Beaucage et al., Deoxynucleoside phosphoramidites—A new class of key intermediates for deoxypolynucleotide synthesis. *Tetrahedron Lett.* 22(20): 1859-62 (1981).
Becker et al., High resolution colonoscopy in live mice. *Nat. Protoc.* 1(6):2900-4 (2006).
Best et al., Development of a Crohn's disease activity index. National Cooperative Crohn's Disease Study. *Gastroenterology* 70(3): 439-44 (1976).
Brown et al., Chemical synthesis and cloning of a tyrosine tRNA gene. *Meth. Enzymol.* 68: 109-51 (1979).
Bustin et al., Quantitative real-time RT-PCR—a perspective. *.J Mol. Endocrinol.* 34: 597-601 (2005).
Bustin, Absolute quantification of mRNA using real time reverse transcription polymerase chain reaction assays. *J. Mol. Endocrinol.* 25: 169-93 (2000).
Campbell et al., Calculating confidence intervals for some non-parametric analyses. *Br. Med. J.* 296: 1454-6 (1988).
Catalucci et al., MicroRNAs in cardiovascular biology and heart disease. *Circ. Cardiovasc. Genet.* 2: 402-8 (2009).
Cheng et al., Antisense inhibition of human miRNAs and indications for an involvement of miRNA in cell growth and apoptosis. *Nucl. Acids Res.* 33(4): 1290-7 (2005).
Cho, MicroRNAs in cancer—from research to therapy. *Biochim. Biophys. Acta.* 1805: 209-17 (2010).
Coskun et al., MicroRNAs in inflammatory bowel disease—pathogenesis, diagnostics and therapeutics. *World J. Gastroenterol.* 18(34): 4629-34 (2012).
Desai et al., Review article: biological activity markers in inflammatory bowel disease. *Aliment Pharmacol. Ther.* 25: 247-55 (2007).
Ebert et al., MicroRNA sponges: competitive inhibitors of small RNAs in mammalian cells. *Nat. Methods* 4: 721-6 (2007).
Ebert et al., MicroRNA sponges: progress and possibilities. *RNA* 16: 2043-50 (2010).
Fasseu et al., Identification of restricted subsets of mature abnormally expressed in inactive colonic mucosa patients with Inflammatory Bowel Disease. 5(10): e13160 (2010).
Gentner et al. Stable knockdown of microRNA in vivo by lentiviral vectors. *Nat. Methods* 6: 63-6) (2009).
Grassl et al., CD34 mediates intestinal inflammation in *Salmonella*-infected mice. *Cell Microbiol.* 12(11): 1562-75 (2010).
Hapfelmeier et al., The *Salmonella* pathogenicity island (SPI)-2 and SPI-1 type III secretion systems allow *Salmonella* serovar typhimurium to trigger colitis via MyD88-dependent and MyD88-independent mechanisms. *J. Immunol.* 174(3): 1675-85 (2005).

(Continued)

*Primary Examiner* — Brian Whiteman
(74) *Attorney, Agent, or Firm* — Marshall, Gerstein & Borun LLP

(57) ABSTRACT

The present invention relates to an in vitro method for diagnosing an acute or relapsing phase of inflammatory bowel disease as well as a method for treating the acute or relapsing phase of inflammatory bowel disease. In addition, the present invention relates to a medicament for use in the treatment of inflammatory bowel disease. Further comprised by the present invention is the use of a nucleic acid molecule of SEQ ID NO: 1 or 2 for monitoring the progression of said disease and in vitro diagnosis of an acute or relapsing phase of said disease. Also a device for the diagnosis of said disease and kits for performing the method of the present invention are envisaged by the present invention.

16 Claims, 18 Drawing Sheets

Figure 1A:
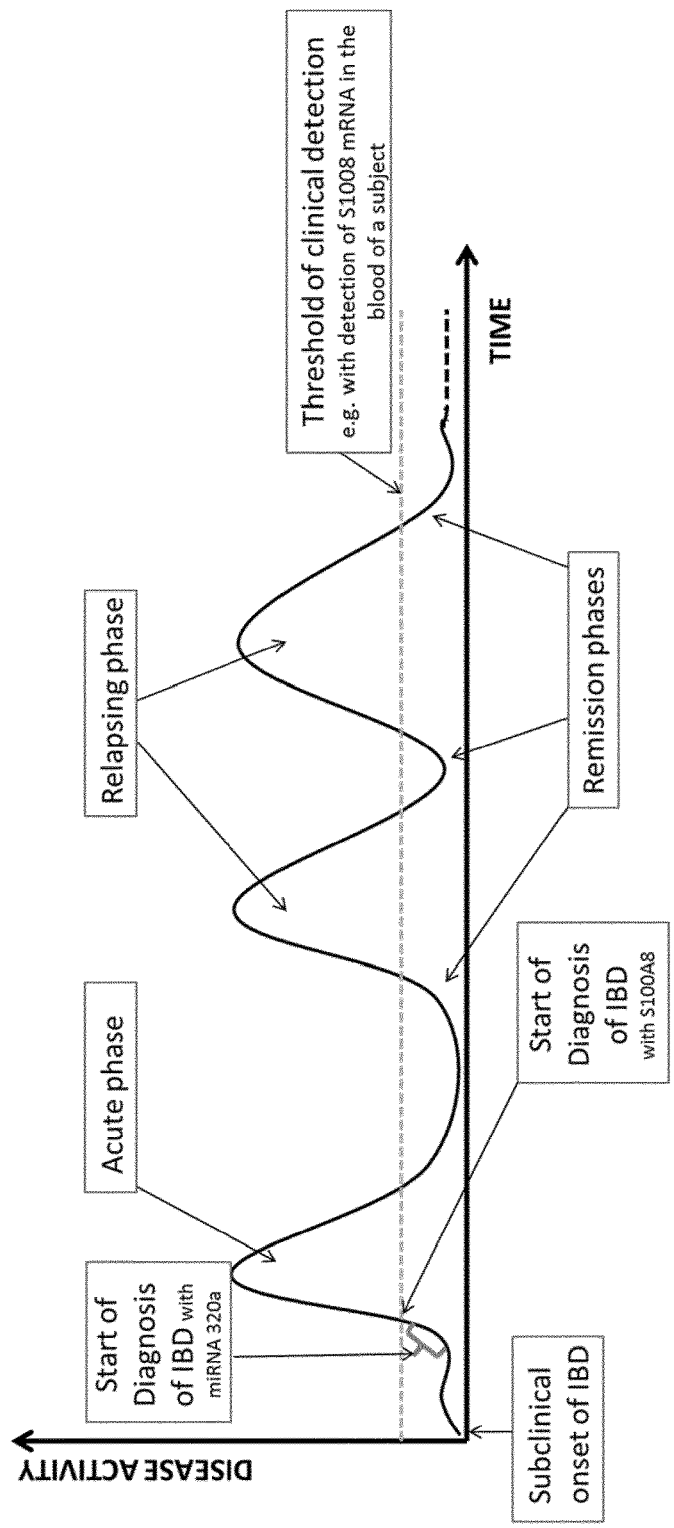

Specification includes a Sequence Listing.

(56) References Cited

OTHER PUBLICATIONS

Invitrogen—Life Technologies, NCode (TM) miRNA first-stand cDNA synthesis and qRT-PCR kits. https://tools.lifetechnologies.com/content/sfs/manuals/ncode_firststrand_qRTPCR_man.pdf , retrieved Mar. 2, 2015.
Jiang et al., MicroRNAs and the regulation of fibrosis. *FEBS J.* 277(9): 2015-21 (2010).
Lewis et al., Conserved seed pairing, often flanked by adenosines, indicates that thousands of human genes are microRNA targets. *Cell* 120: 15-20 (2005).
Matteucci et al., Synthesis of deoxyoligonucleotides on a polymer support. *Am. Chem. Soc.* 103: 3185-91 (1981).
Nakasa et al., Expression of microRNA-146 in rheumatoid arthritis synovial tissue. *Arthritis Rheum.* 58: 1284-92 (2008).
Narang et al., Improved phosphotriester method for the synthesis of gene fragments. *Methods Enzymol.* 68: 90-8 (1979).
Nielsen et al., New strategies for treatment of inflammatory bowel disease. *Front. Med.* 1: 3 (2014).
Nell et al., the impact of the microbiota on the pathogenesis of IBD: lessons from mouse infection models. *Nat. Rev. Microbiol.* 8(8): 564-77 (2010).
Ostanin et al., T cell-induced inflammation of the small and large intestine in immunodeficient mice. *Am. J. Physiol. Gastrointest. Liver Physiol.* 290(1): G109-19 (2006).
Pekow et al., MicroRNA in inflammatory bowel disease. *Inflamm. Bowel Dis.* 18(1): 187-93 (2012).
Peltier et al., Normalization of microRNA expression levels in quantitative RT-PCR assays: Identification of suitable reference RNA targets in normal and cancerous human solid tissues. *RNA* 14(5): 844-52 (2008).
Perron et al., Regulatory RNAs: Future perspectives in diagnosis, prognosis, and individualized therapy. *Methods Mol. Biol.* 361: 311-26 (2006).
Perše et al., Dextran sodium sulphate colitis mouse model: traps and tricks. *J. Biomed. Biotechnol.* 2012: 718617 (2012).
Rizzello et al., Review article: monitoring activity in ulcerative colitis. *Aliment Pharmacol. Ther.* 16(Suppl. 4): 3-6 (2002).
Shi et al., Direct reverse transcription—polymerase chain reaction from whole blood without RNA extraction. *Genet. Anal. Tech. Appl.* 9(5-6): 149-50 (1992).
Sonkoly et al., MicroRNAs: novel regulators involved in the pathogenesis of psoriasis? *PLoS One* 2: e610 (2007).
Stanczyk et al. Altered expression of MicroRNA in synovial fibroblasts and synovial tissue in rheumatoid arthritis. *Arthritis Rheum.* 58: 1001-9 (2008).
Stecher et al., Comparison of *Salmonella enterica* serovar Typhimurium colitis in germfree mice and mice pretreated with streptomycin. *Infect. Immun.* 73(6): 3228-41 (2005).
Stenvang et al., Inhibition of microRNA function by antimiR oligonucleotides. *Silence* 3(1): 1 (2012).
Tan et al., Allele-specific targeting of microRNAs to HLA-G and risk of asthma. *Am. J. Hum. Genet.* 81: 829-34 (2007).
Tang et al., Role of microRNAs in diabetes. *Biochim. Biophys. Acta* 1779(11): 697-701 (2008).
Travis et al., Review article: Defining remission in ulcerative colitis. *Aliment Pharmacol Ther.* 34(2): 113-24 (2011).
Truelove et al., Cortisone in ulcerative colitis: Preliminary report on a therapeutic trial. *Br. Med. J.* 2(4884): 375-8 (1954).
Truelove et al., Intensive intravenous regimen for severe attacks of ulcerative colitis. *Lancet* 1(7866): 1067-70 (1974).
Van Rooij, The art of microRNA research. *Circ. Res.* 108: 219-34 (2011).
Waldner et al., Confocal laser endomicroscopy and narrow-band imaging-aided endoscopy for in vivo imaging of colitis and colon cancer in mice. *Nat. Protoc.* 6(9): 1471-81 (2011).
Wu et al., Peripheral blood microRNAs distinguish active ulcerative colitis and Crohn's disease. *Inflamm. Bowel Dis.* 17(1): 241-50 (2011).
Żyżńska-Granica et al., Identification of suitable reference genes for real-time PCR analysis of statin-treated human umbilical vein endothelial cells. *PLoS One* 7(12): e51547 (2012).

* cited by examiner

Figure 1B
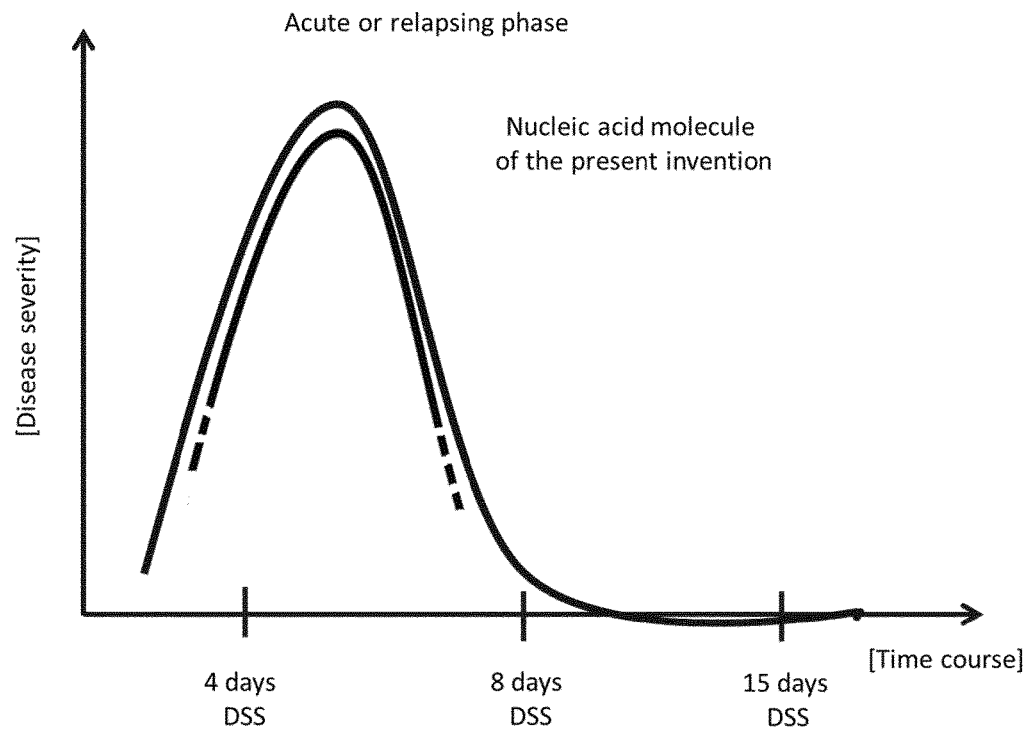
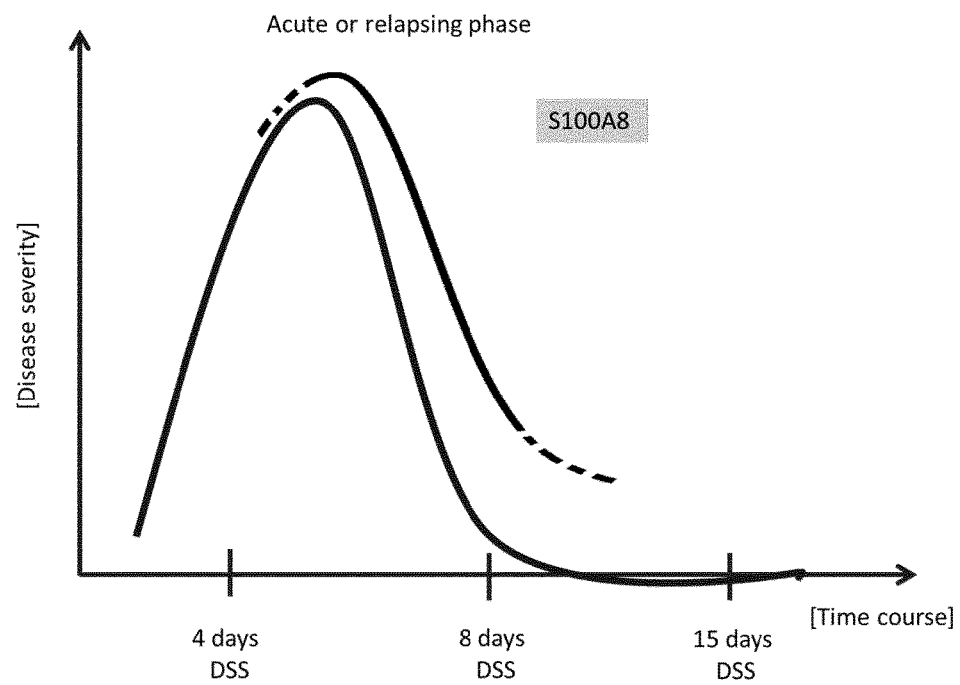

Figure 2B, C
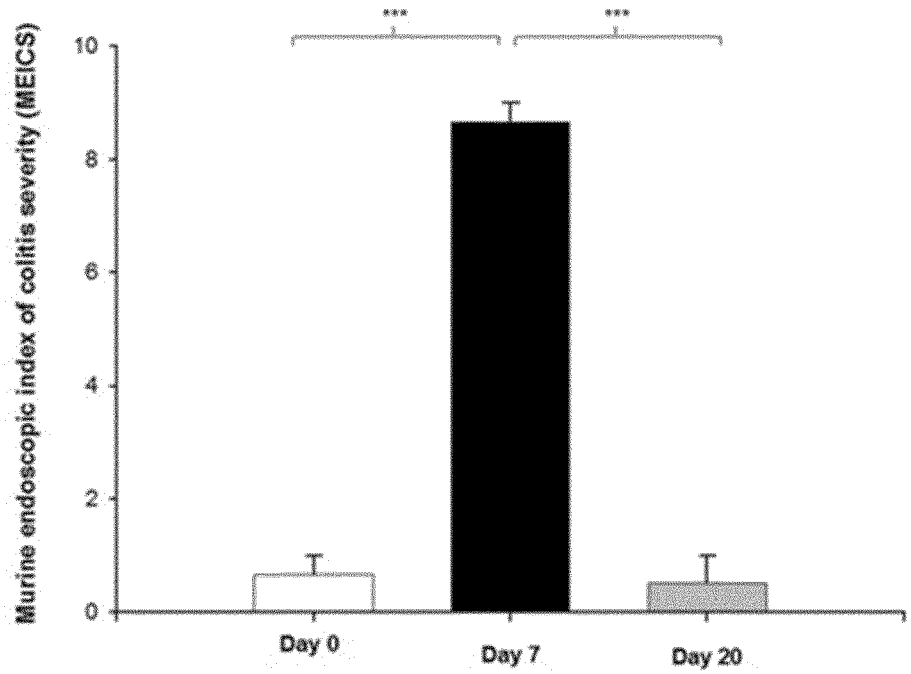
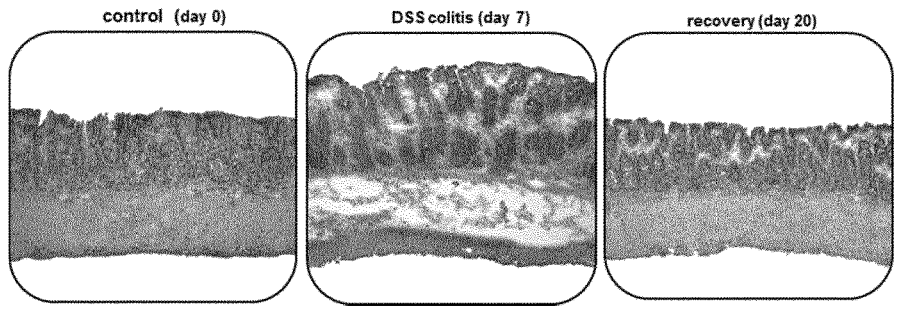
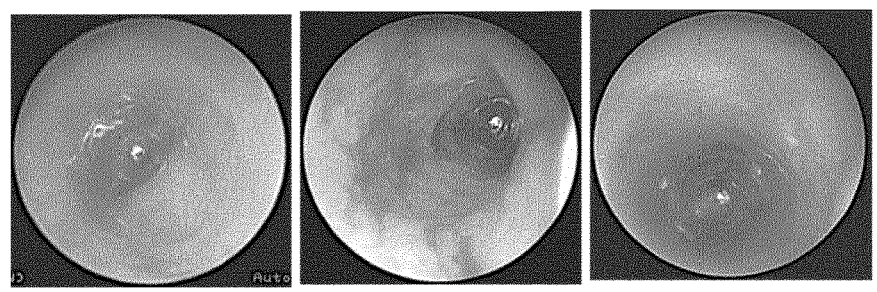

Figure 3A, B
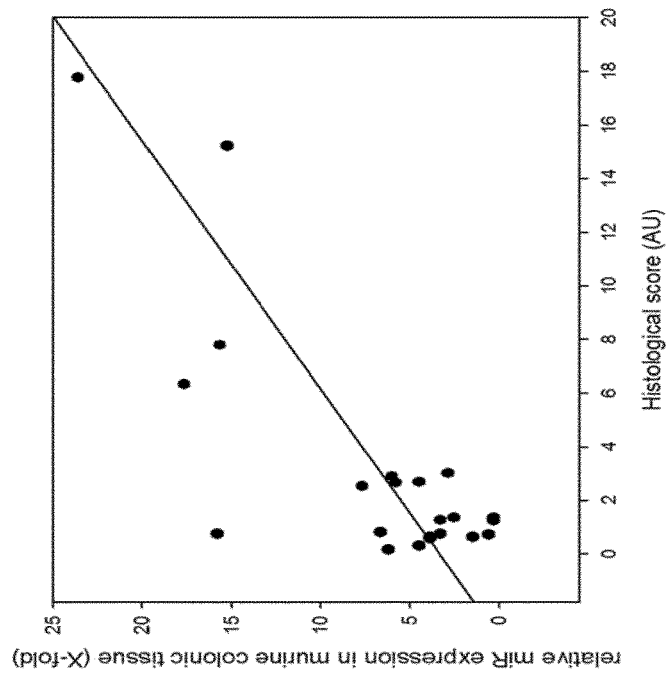
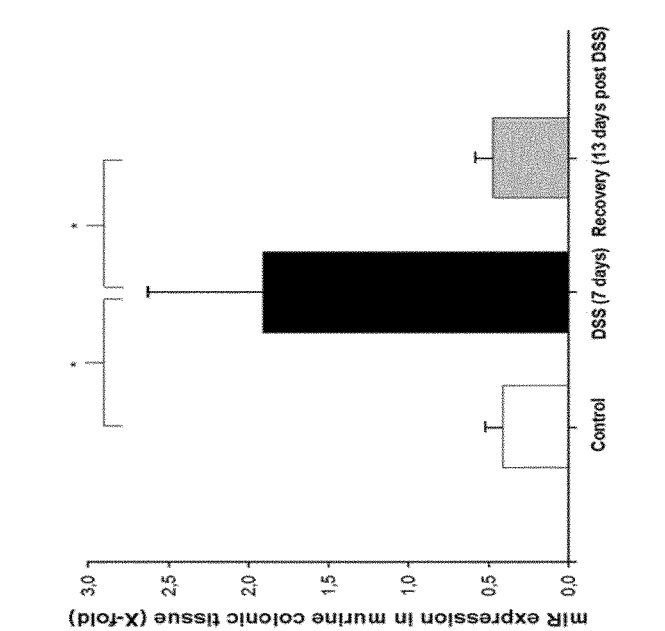

Figure 3C, D
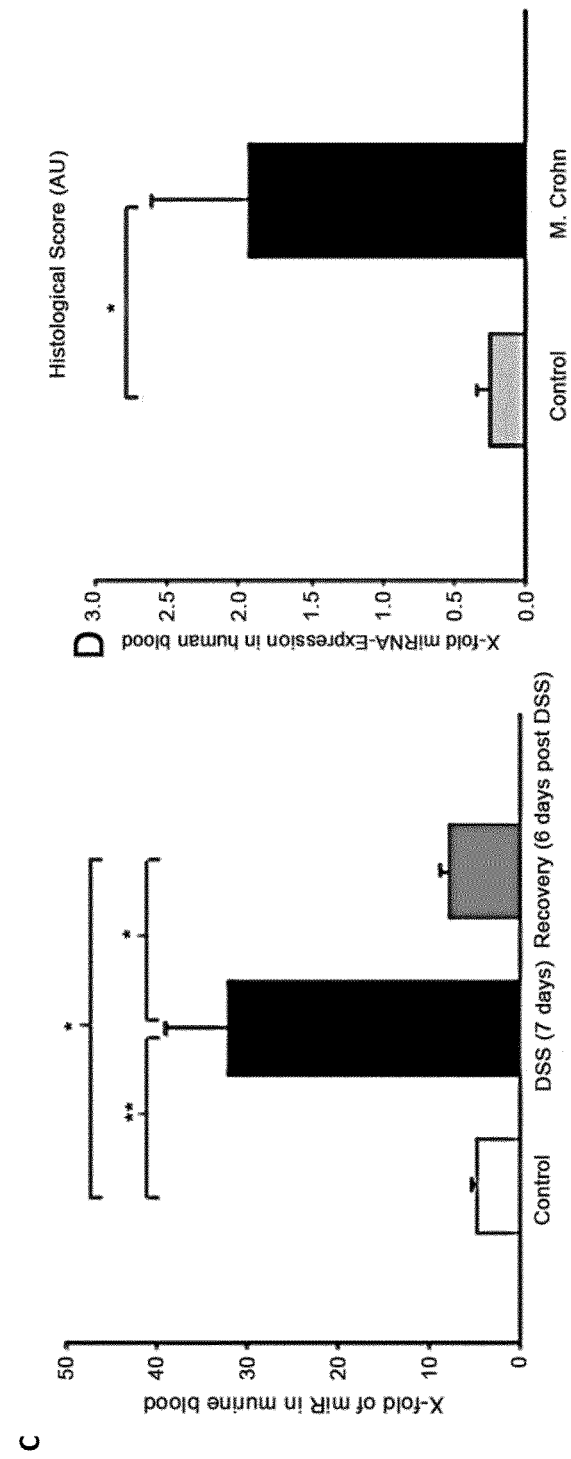

SEQUENCE LISTING

```
<160> NUMBER OF SEQ ID NOS: 5

<210> SEQ ID NO 1
<211> LENGTH: 22
<212> TYPE: DNA
<213> ORGANISM: Unknown
<220> FEATURE:
<223> OTHER INFORMATION: this sequence is the same in different animals

<400> SEQUENCE: 1
aaaagcuggg uugagagggc ga                                              22

<210> SEQ ID NO 2
<211> LENGTH: 23
<212> TYPE: DNA
<213> ORGANISM: Sus scrofa

<400> SEQUENCE: 2
aaaagcuggg uugagagggc gaa                                             23

<210> SEQ ID NO 3
<211> LENGTH: 21
<212> TYPE: DNA
<213> ORGANISM: Artificial Sequence
<220> FEATURE:
<223> OTHER INFORMATION: Primer 1 S100A8_for

<400> SEQUENCE: 3
cttcccacac gtgtatccct a                                               21

<210> SEQ ID NO 4
<211> LENGTH: 21
<212> TYPE: DNA
<213> ORGANISM: Artificial Sequence
<220> FEATURE:
<223> OTHER INFORMATION: Primer 2 S100A8_rev

<400> SEQUENCE: 4
ccaaataacc aaaccagcag a                                               21

<210> SEQ ID NO 5
<211> LENGTH: 22
<212> TYPE: DNA
<213> ORGANISM: Artificial Sequence
<220> FEATURE:
<223> OTHER INFORMATION: Hs_miR-320a_1

<400> SEQUENCE: 5
aaaagcuggg uugagagggc ga                                              22
```

MIRNA 320A AS BIOMARKER FOR INFLAMMATORY BOWEL DISEASE

FIELD OF THE INVENTION

The present invention relates to an in vitro method for diagnosing an acute or relapsing phase of inflammatory bowel disease as well as a method for treating the acute or relapsing phase of inflammatory bowel disease. In addition, the present invention relates to a medicament for use in the treatment of inflammatory bowel disease. Further comprised by the present invention is the use of a nucleic acid molecule of SEQ ID NO: 1 or 2 for monitoring the progression of said disease and in vitro diagnosis of an acute or relapsing phase of said disease. Also a device for the diagnosis of said disease and kits for performing the method of the present invention are envisaged by the present invention.

BACKGROUND OF THE INVENTION

Inflammatory bowel diseases (IBD), such as Crohn's disease (CD) and ulcerative colitis (UC) are severe and relapsing immunologically mediated chronic disorders of the gastrointestinal tract. IBDs are heterogeneous diseases characterized by various genetic abnormalities that lead to overly aggressive inflammatory responses to a subset of commensal enteric bacteria.

Crohn's disease can affect all parts of the digestive tract and specially the ileum and/or colon and leads to mucosal ulcerations, fistula, and deep infiltration of inflammatory cells in the bowel wall.

Ulcerative colitis often involves the lower part of the colon and the rectum and mucosal inflammation may extend to the caecum in a contiguous pattern.

The diagnosis of inflammatory bowel disease (IBD) is often achieved only months or years after the onset of symptoms. Several serological indicators of IBD have been identified; in general, they are antibodies directed against antigens expressed by organisms of the intestinal microbiome. For example, the anti-Saccharomyces cerevisiae antibody (ASCA) interacts with mannose epitopes of this yeast species and is present in 48% to 80% of patients with CD (Barahona-Garrido et al., (2009) Serological markers in inflammatory bowel disease: a review of their clinical utility. Rev Gastroenterol Mex.74(3):230-7). In general, these markers are specific for IBD, but experience low sensitivity. IBD biomarkers can also be of value after the diagnosis is established, as measures of disease activity and predictors of outcome. So far, endoscopy used in the diagnosis of IBD can be accurate but is invasive and expensive. Hence, there is still a need for biological markers of disease activity, which are simple to use in clinical practice, reliable and inexpensive.

Other serum and stool markers, such as C-reactive protein (CRP) and fecal calprotectin, are elevated in inflammatory and gastrointestinal diseases, but are not all specific for IBD (Desai, Fabion and Sandborn (2007) Review article: biological activity markers in inflammatory bowel disease. Aliment Pharmacol Ther 25, 247-255). The introduction of additional sensitive, specific, and noninvasive diagnostic markers may aid in the diagnosis of IBD, reduce patient risk and discomfort by reducing invasive testing, and accelerate the study of new treatments. One possibility is that miRNAs may serve as biomarkers for IBD.

MicroRNAs (miRNAs) are small (~22-24 nucleotide), noncoding RNAs that act as key regulators of gene expression (Guarnieri D J, DiLeone R J. MicroRNAs: a new class of gene regulators. Ann Med. 2008; 40:197-208). Briefly, they are initially transcribed as longer primary miRNA transcripts in the nucleus then subsequently processed by Drosha and DGCR8 into precursor miRNA (pre-miRNA). The pre-miRNA is exported to the cytoplasm by exportin 5 in a ras-related nuclear protein guanosine triphosphate-dependent manner. The cytoplasmic pre-miRNA is cleaved by Dicer and the functional miRNA strand incorporated into the RNA-inducing silencing complex (RISC). Once loaded, the miRNA binds to complementary sequences in the 3'-untranslated region (3'UTR) of target miRNAs, resulting in suppression of translation and/or degradation of mRNA.

Overall, miRNAs are thought to contribute to the regulation of over 60% of all protein coding genes (Lewis Burge, Bartel (2005) Conserved seed pairing, often flanked by adenosines, indicates that thousands of human genes are microRNA targets. Cell:120:15-20) including those involved in development, metabolism, cell cycle control and fibrosis (Guarnieri D J, DiLeone; Jiang X, Tsitsiou E, Herrick S E, et al. (2010) MicroRNAs and the regulation of fibrosis. FEBS J:277:2015).

It has been hypothesized that the differential expression of miRNAs may distinguish disease states (Perron M P, Boissonneault V, Gobeil L A, et al. (2006) Regulatory RNAs: Future Perspectives in Diagnosis, Prognosis, and Individualized Therapy. Methods Mol Biol:361:311-326). Indeed, altered miRNA profiles have been noted a vast array of diseases including multiple cancer subtypes (Cho W C. (2010) MicroRNAs in cancer—from research to therapy. Biochim Biophys Acta:1805:209-217) cardiovascular diseases (Catalucci D, Gallo P, Condorelli G. (2009) MicroRNAs in cardiovascular biology and heart disease. Circ Cardiovasc Genet:2:402-408), diabetes (Tang X, Tang G, Ozcan S. (2008) Role of microRNAs in diabetes. Biochim Biophys Acta:1779:697-701), and several inflammatory and autoimmune diseases (Sonkoly E, Wei T, Janson P C, et al. (2007) MicroRNAs: novel regulators involved in the pathogenesis of Psoriasis? PLoS One:2:e610; Stanczyk J, Pedrioli D M, Brentano F, et al. (2008) Altered expression of MicroRNA in synovial fibroblasts and synovial tissue in rheumatoid arthritis. Arthritis Rheum:58:1001-1009; Nakasa T, Miyaki S, Okubo A, et al. (2008) Expression of microRNA-146 in rheumatoid arthritis synovial tissue. Arthritis Rheum:58: 1284-1292; Tan Z, Randall G, Fan J, et al. (2007) Allele-specific targeting of microRNAs to HLA-G and risk of asthma. Am J Hum Genet:81:829-834), including CD and UC (Wu et al., (2011) Peripheral blood microRNAs distinguish active ulcerative colitis and Crohn's disease. Inflamm Bowel Dis. 17(1): 241-250).

Wu et al profiled miRNA expression in blood of ulcerative colitis (UC) and Crohn's disease (CD) patients, namely active CD, inactive CD, active UC, inactive UC. Specifically, the blood expression of miRs-199a-5p, -362-3p, -340*, -532-3p and miRplus-1271 were elevated in both CD and UC as compared to healthy controls. In addition, miRs-28-5p, -151-5p, -199a-5p, -340* and miRplus-E1271 were increased in the peripheral blood of patients with active UC but not in inactive UC and miRs-199a-5p, -362-3p and -532-3p and miRplus-E1271 were increased in the peripheral blood of patients with active CD but not in the blood of patients with inactive CD as compared to healthy controls.

Fasseu et al., describes dysregulated miRNAs in colonic pinch biopsies in CD and UC (Fasseu et al., (2010) Identification of Restricted Subsets of Mature Abnormally Expressed in Inactive Colonic Mucosa Patients with Inflammatory Bowel Disease. Volume 5, Issue 10, e13160).

Similarly, Coskun et al. summarizes dysregulated miR-NAs in IBD (Coskun et al., (2012) MicroRNAs in inflammatory bowel disease—pathogenesis, diagnostics and therapeutics. World J Gastroenterol; 18(34): 4629-4634). Also WO 2009/120877 describes differentaly regulated miRNAs in CD and UC from blood and biopsis.

An object of the present was therefore to provide an alternative method for detecting UC and CD.

The technical problem is solved by the embodiments reflected in the claims, described in the description, and illustrated in the Examples and Figures.

The above being said, the present invention relates to an in vitro method for diagnosing an acute or relapsing phase of inflammatory bowel disease in a subject, the method comprising
  i) determining the level of a nucleic acid molecule comprising any one of SEQ ID NO: 1 or 2 in a test sample;
  ii) comparing the level of the nucleic acid molecule determined in the test sample with a control sample;
    wherein an elevation of said nucleic acid molecule in the test sample is indicative of an acute or relapsing phase of said inflammatory bowel disease.

In one embodiment of the method of the present invention, the nucleic acid molecule has the SEQ ID NO: 1.

In another embodiment of the method of the present invention, the subject is a mammal, preferably a human being.

In another embodiment of the method of the present invention, the level of the S100A8 mRNA in said subject exhibits no alteration when compared to the control subject.

In another embodiment of the method of the present invention, the method further comprises the step of determining the S100A8 mRNA level in said test sample and optionally comparing it to the level in the control sample.

In another embodiment of the method of the present invention, the test sample and/or said control sample is any sample obtained not using endoscopy.

In another embodiment of the method of the present invention, the test sample and/or said control sample is selected from stool, urine, blood, salvia, preferably the test and/or control sample is a blood sample.

In another embodiment of the method of the present invention, the level of said nucleic acid molecule is determined by qRT-PCR.

In another embodiment of the method of the present invention, the level of S100A8 is determined by qRT-PCR.

In another embodiment of the method of the present invention, the method comprises the steps of
  a) extracting RNA from the test sample;
  b) performing qRT-PCR with specific oligonucleotides suitable to detect said nucleic acid molecule.

In another embodiment of the method of the present invention, the level of the nucleic acid molecule is detected by a method comprising:
  a) extracting RNA from said test sample;
  b) treating the obtained RNA with a reverse transcription reaction mixture comprising specific oligonucleotides corresponding to the nucleic acid molecule of SEQ ID NO: 1 or 2, dNTPs and a reverse transcriptase under conditions allowing transcription of the nucleic acid molecule into complementary DNA (cDNA);
  c) quantitative detection of cDNA transcripts of said nucleic acid molecule, wherein steps b) and c) can be either performed in separate reactions or in one reaction.

The present invention further relates to a method for diagnosing the acute or relapsing phase of inflammatory bowel disease comprising:
  (a) determining the level of SEQ ID NO: 1 or 2 in a test sample;
  (b) determining the level of S100A8 mRNA in said test sample; and
  (c) comparing both levels to a control sample or control value;
  wherein an increase of said SEQ ID and no alteration of said S100A8 in comparison to said control sample or control value indicates the acute or relapsing phase of inflammatory bowel disease.

The present invention also relates to a method for treating the acute or relapsing phase of inflammatory bowel disease in a subject comprising:
  (a) determining the level of any of SEQ ID NO: 1 or 2 in a test sample;
  (b) determining the level of S100A8 mRNA in said test sample;
  (c) comparing both levels to a control sample or control value; and
  (d) treating said subject with MEDICAMENT, provided that said test sample is characterized by an increase of said SEQ ID and by no alteration of said S100A8 in comparison to said control sample or control value.

Additionally, the present invention relates to a MEDICAMENT for use in the treatment of inflammatory bowel disease in a subject, wherein said subject is characterized by an increase of SEQ ID NO: 1 or 2 and by no alteration of S100A8 mRNA in comparison to a control subject or control value.

The present invention also relates to the use of the level of SEQ ID NO: 1 or 2 in a test sample of a subject suffering from inflammatory bowel disease, for monitoring the progression of said disease in said subject.

Further, the present invention relates to a use of a nucleic acid molecule selected of any of SEQ ID NO: 1 or 2 for in vitro diagnosis of an acute or relapsing phase of inflammatory bowel disease.

In one embodiment, the use of the nucleic acid molecule selected of any of SEQ ID NO: 1 or 2 for in vitro diagnosis includes a subject that has an unchanged expression of S100A8 mRNA as compared to a control subject, preferably the control subject is a healthy subject.

The present invention also relates to a device for the diagnosis of an acute or relapsing phase of inflammatory bowel disease of a subject, wherein the device comprises oligonucleotide sequences to which any of SEQ ID NO: 1 or 2 hybridizes to detect the level of a nucleic acid molecule of SEQ ID NO: 1 or 2 in a test sample.

Additionally, the present invention relates to a kit comprising one or more extraction buffer/reagents and protocol; reverse transcription buffer/reagents and protocol; and qPCR buffer/reagents and protocol suitable for performing any of the methods of the present invention.

FIGURES

FIG. 1A: Theoretical development of IBD with alternating phases of relapse and remission of IBD vs the according miRNA-320a expression.

FIG. 1B: Theoretical marker expression in acute and relapsing phase of IBD. Comparison between SEQ ID NO: 1 or 2 and S100A8.

Figure 1C:
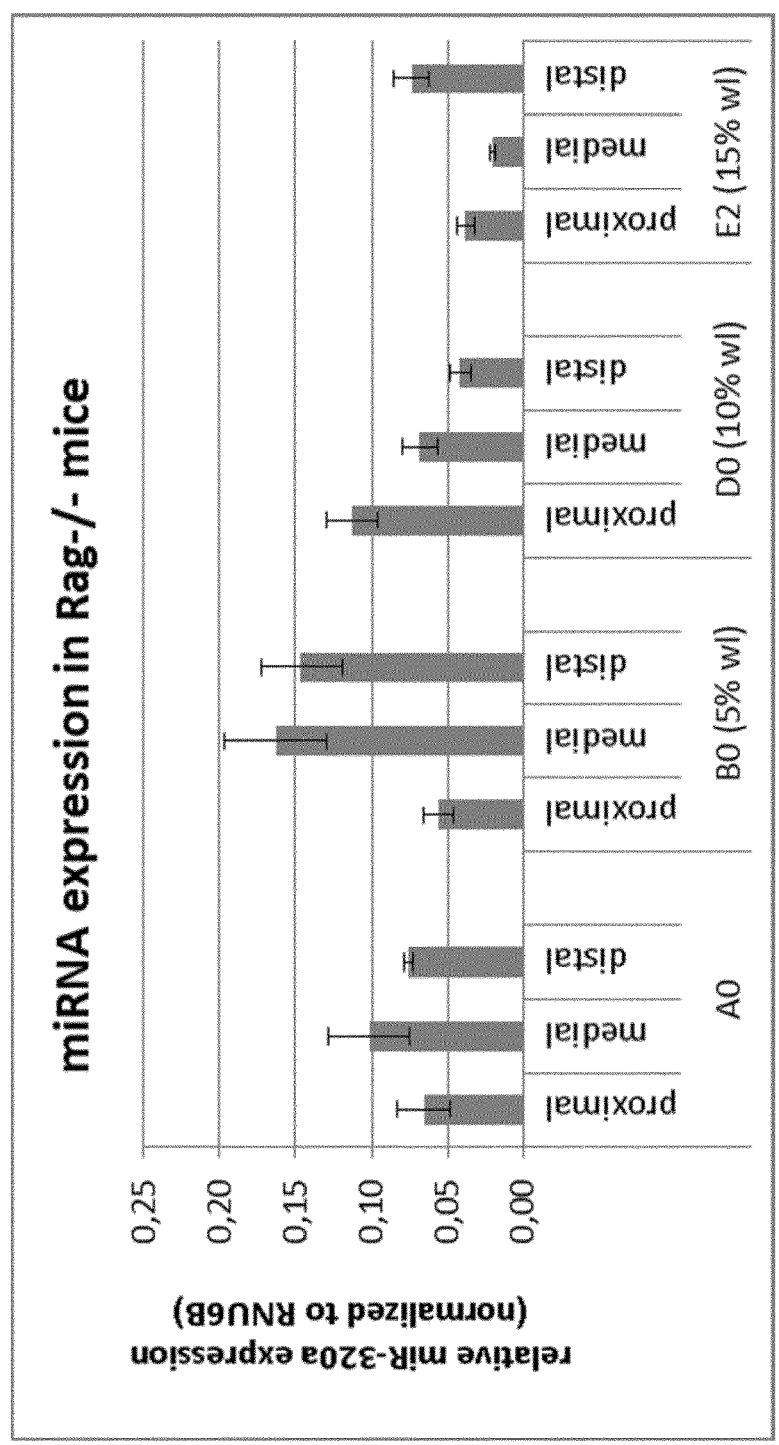

FIG. 1C: In particular in the early phase of disease development (5% weight loss) the miR-320a marker is expressed in defined regions of the colon (medial- and distal part). Relative expression of miR-320a is normalized to the ubiquitously expressed small RNA RNU6B.

Figure 2A:
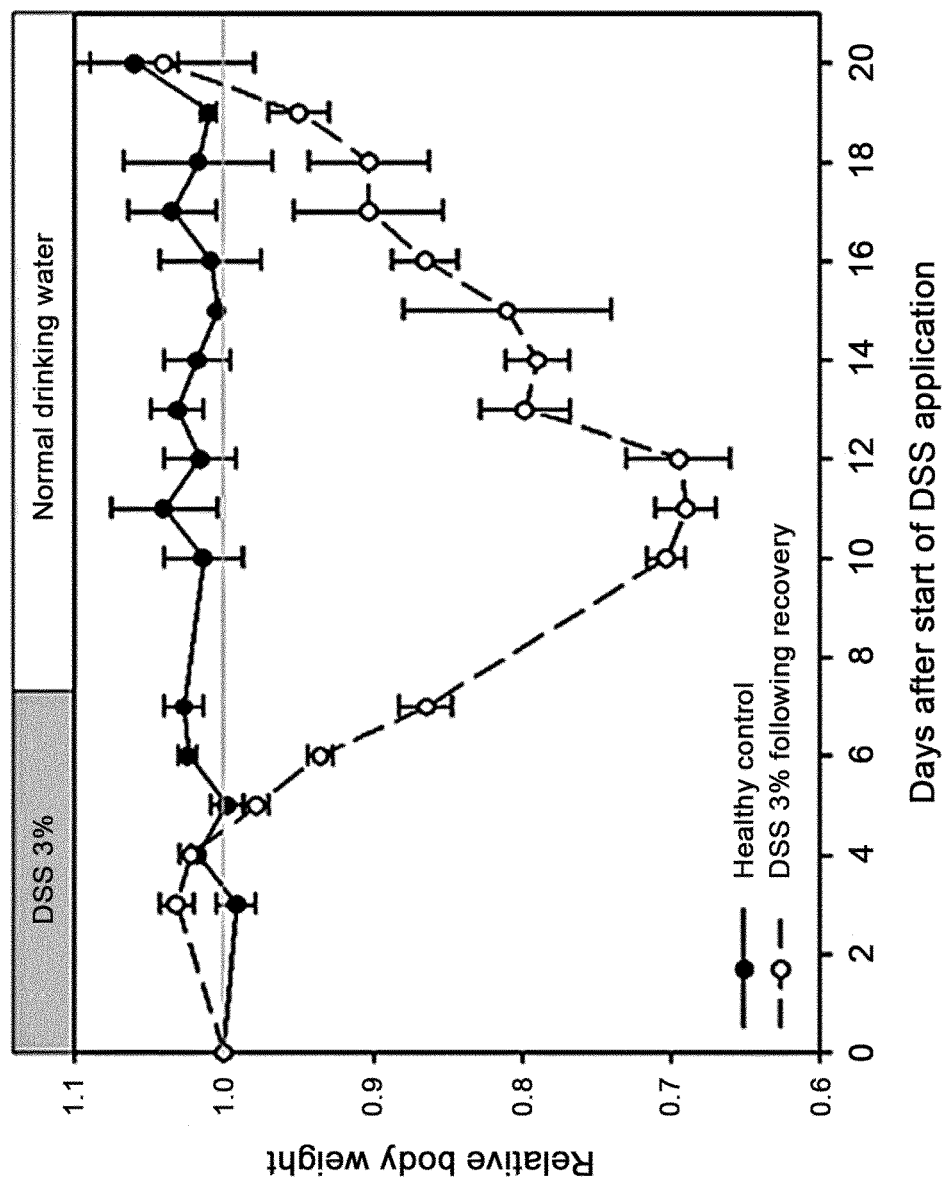

FIG. 2A: Weight curve of mice during development of DSS colitis. On day 7, DSS-treated mice revealed a significant loss of body weight as compared to control mice (81%±2.3 vs. 103%±1.6; P=0.006).

FIG. 2B: The "Murine Endoscopic Index of Colitis Severity index" (MEICS) was significantly increased at day 7 (0.7±0.3 vs. 7.3±0.4; P<0,001).

FIG. 2C: Accordingly, the histological damage at day 7 was markedly increased as compared to controls. The comparison of H&E staining of tissue sections and direct mouse endoscopies are shown.

Figure 2D:
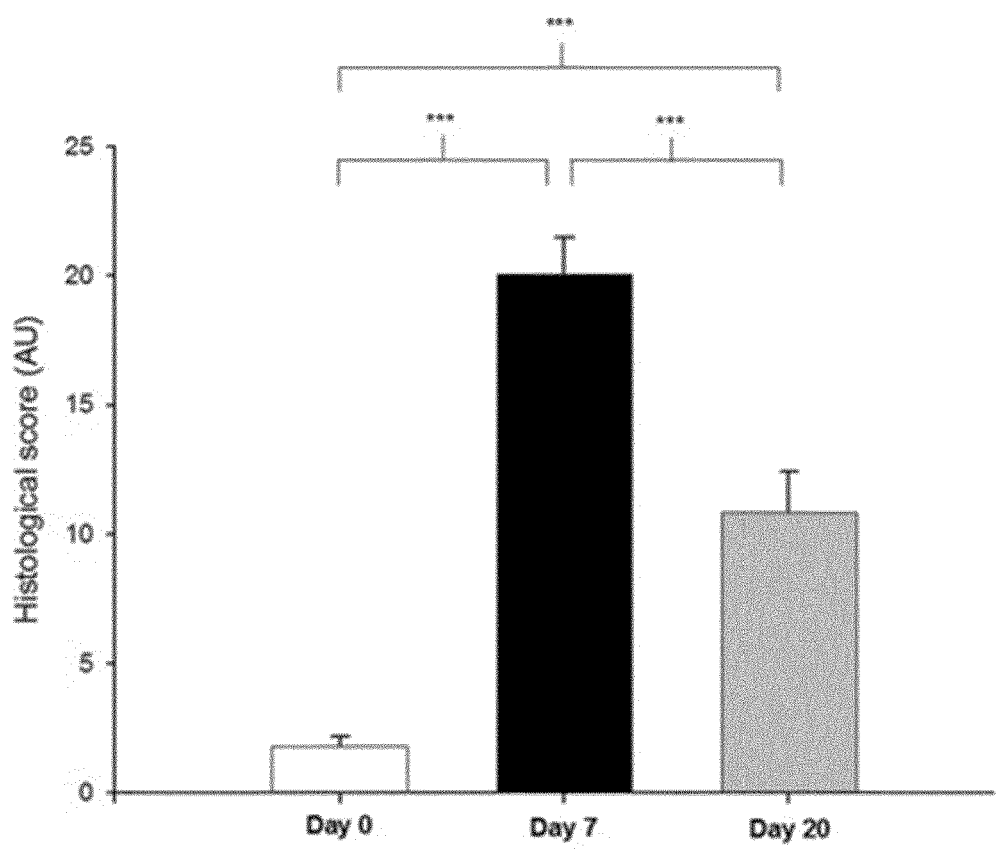

FIG. 2D: Analysis of histological damage: Histological score: Control vs. day 7 after DSS application: (0.5±0.2 vs. 21.7±8.2; P=0.001). At day 13, endoscopic signs of inflammation were markedly ameliorated (MEICS 0,5±0.5) with a reduced histological damage as compared to day 7 (14.5±2.8 vs. 21.7±8.2; P<0.05).

FIGS. 3A and B: Expression of miR-320a during the time course of DSS colitis and "recovery" phase in tissue samples and the statistical correlation of miRNA expression vs. the histological score.

In accordance with the massive histological damage, mucosal expression of miR-320a in the distal colon of colitic mice was significantly increased as compared to healthy controls (0.51±0.08 vs. 0.38±0.01; P=0.04). Furthermore, miR-320a expression in the whole colonic tissue correlated strongly with the severity of histological damage (r 2=0.73; P<0.05).

FIGS. 3C and D: Comparision of miRNA expression in mouse and human blood samples.

In human blood from Crohn's disease patients with an acute flare, miR-320a expression was significantly increased as compared to healthy controls (0.25±0.17 vs. 1.9±1.15; P=0.03).

Figure 4A:
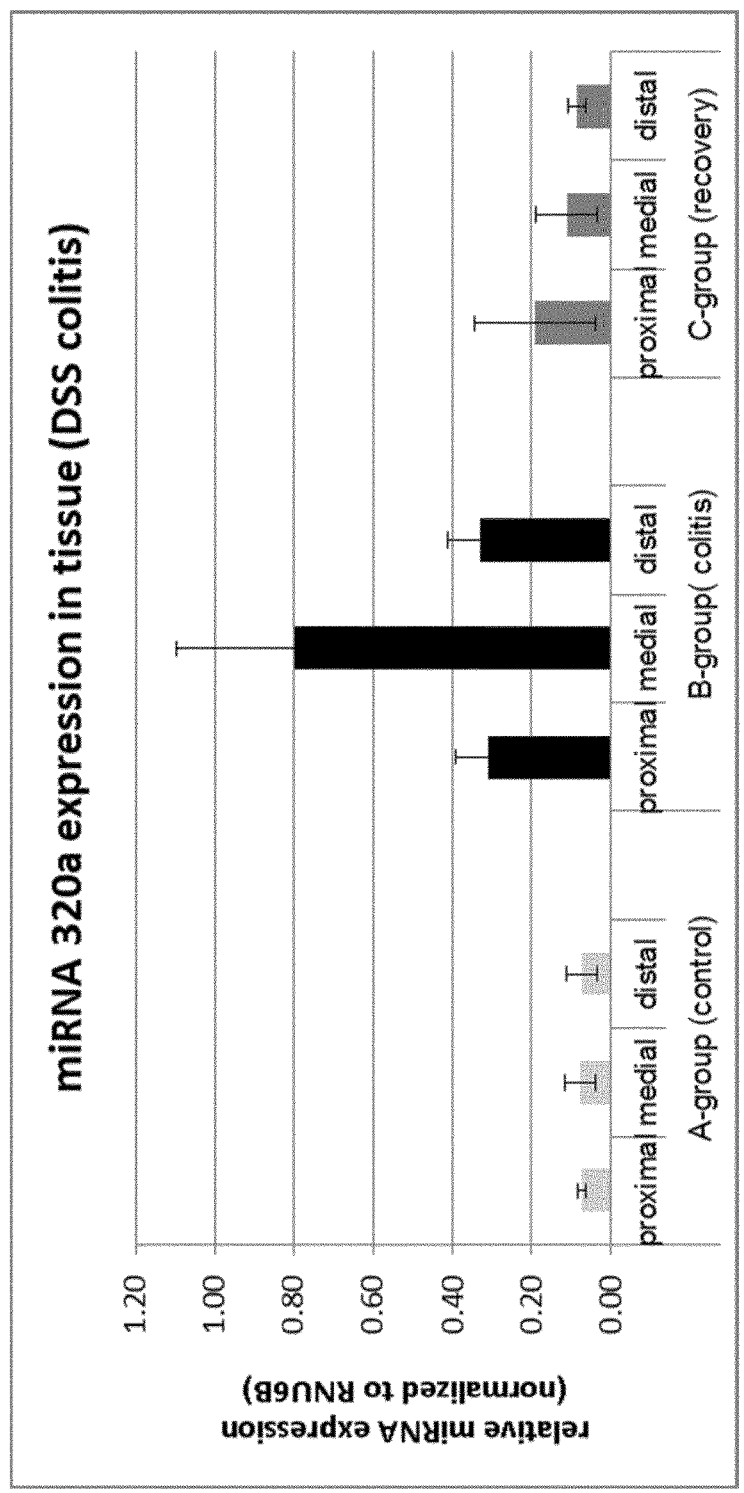

FIG. 4A: MicroRNA expression analysis in colon samples of DSS colitis in mice. Tissue samples were taken from different part of the colon (proximal, medial and distal) as well as at different points in time during disease development: "A group": No DSS in the drinking water for the whole experiment, "B group": DSS application until day 7, development of severe colitis, "C group": DSS was removed from drinking water at day 7 and the animals were able to recover from the disease until day 14 (see also FIG. 2A: weight curve).

Figure 4B:
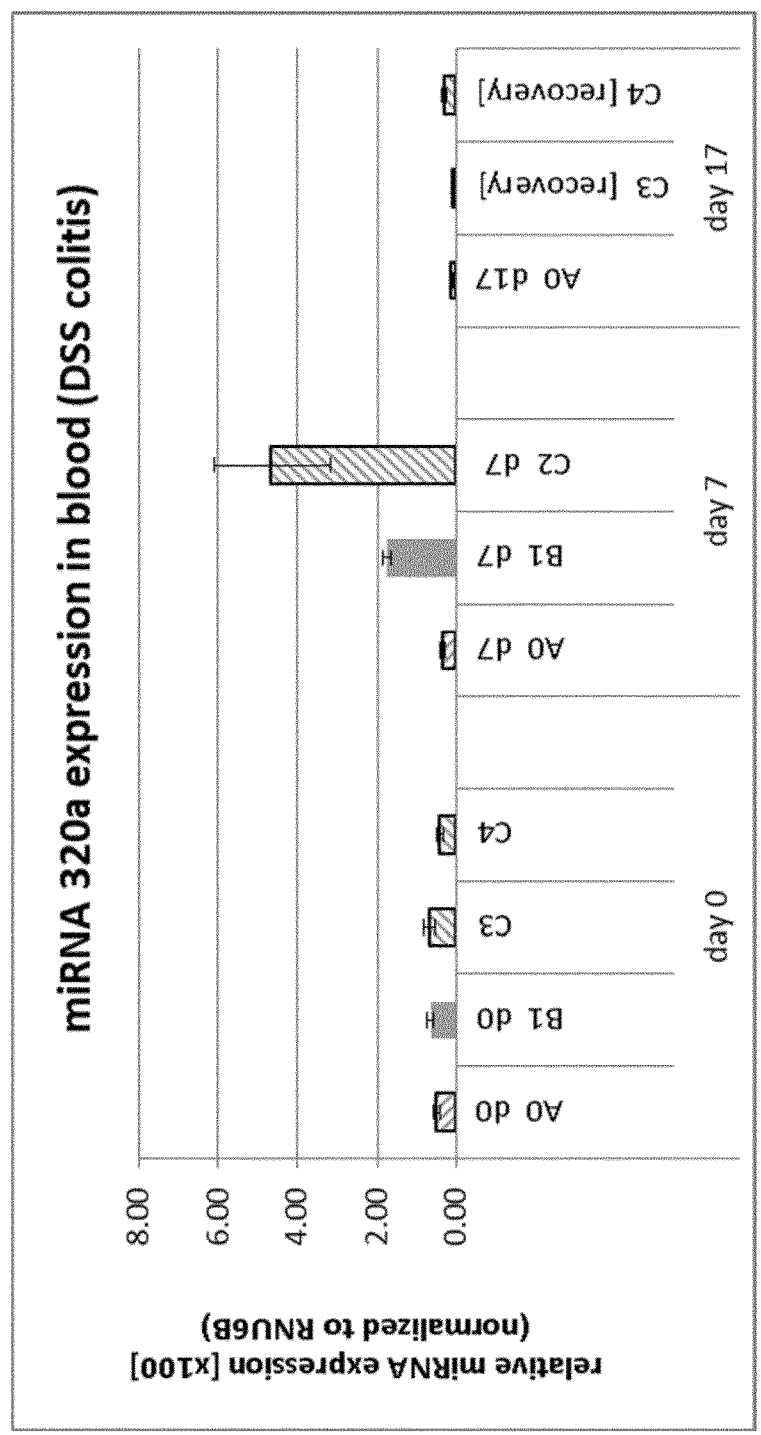

FIG. 4B: MicroRNA expression in blood samples from different DSS colitis mice: "A": mice belong to the control group, "B": mice from the colitis group and "C" : mice from the recovery group.

The miR-320a expression strongly correlates between expression in tissue and blood samples.

Figure 4C:
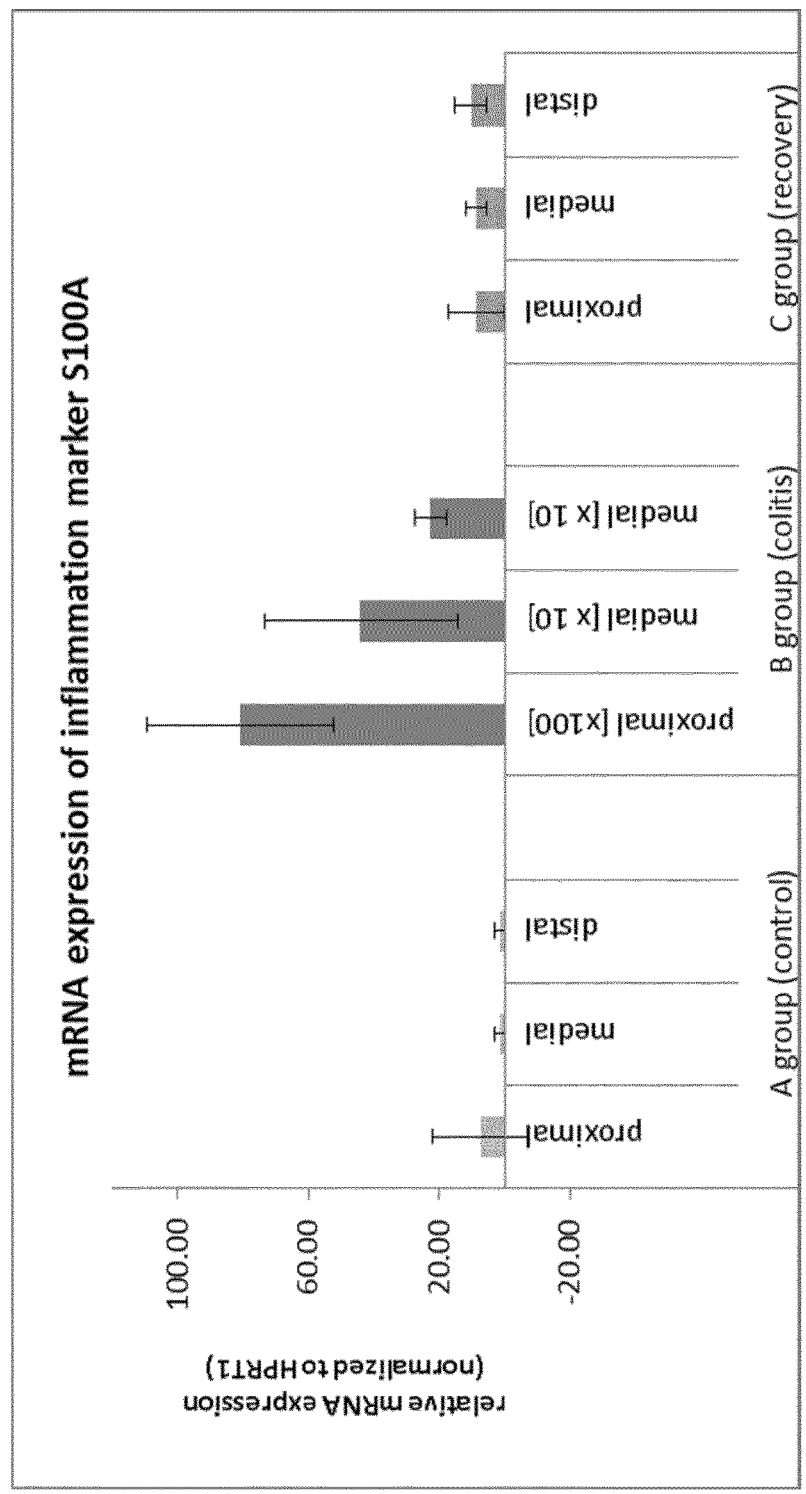

FIG. 4C: The expression of the "inflammation marker" S100A8 (calprotectin) correlates with the time course of miRNA-320 expression in the accordant tissue samples. Relative expression of S100A8 mRNA is normalized to the low expressed housekeeping gene HPRT1.

Figure 4D:
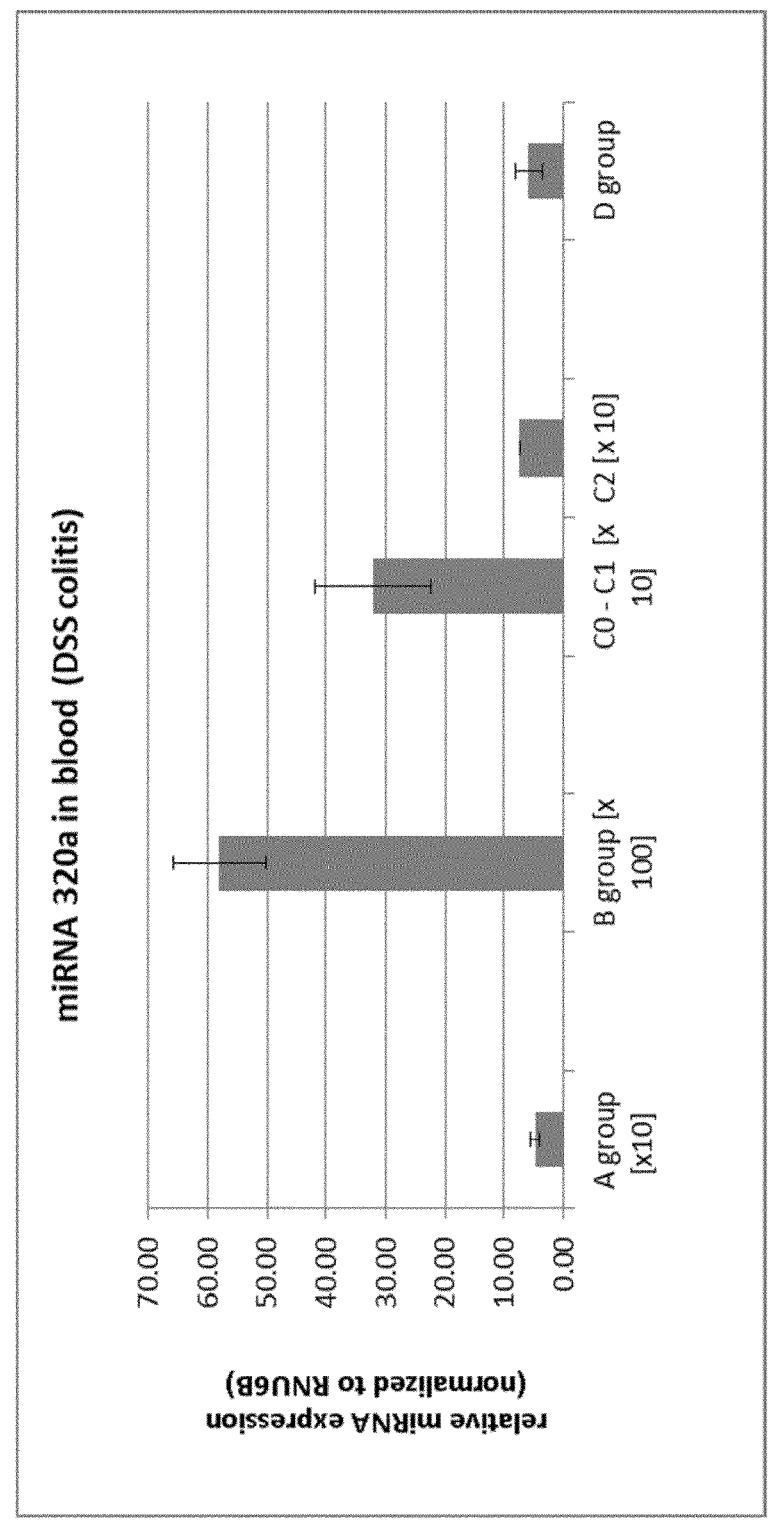

FIG. 4D: The expression of the miRNA320a in blood samples. "A group": No DSS in the drinking water for the whole experiment, "B group": DSS application until day 4, "B group": DSS application until day 8, development of severe colitis, "D group": 15 days recovery.

Figure 4E:
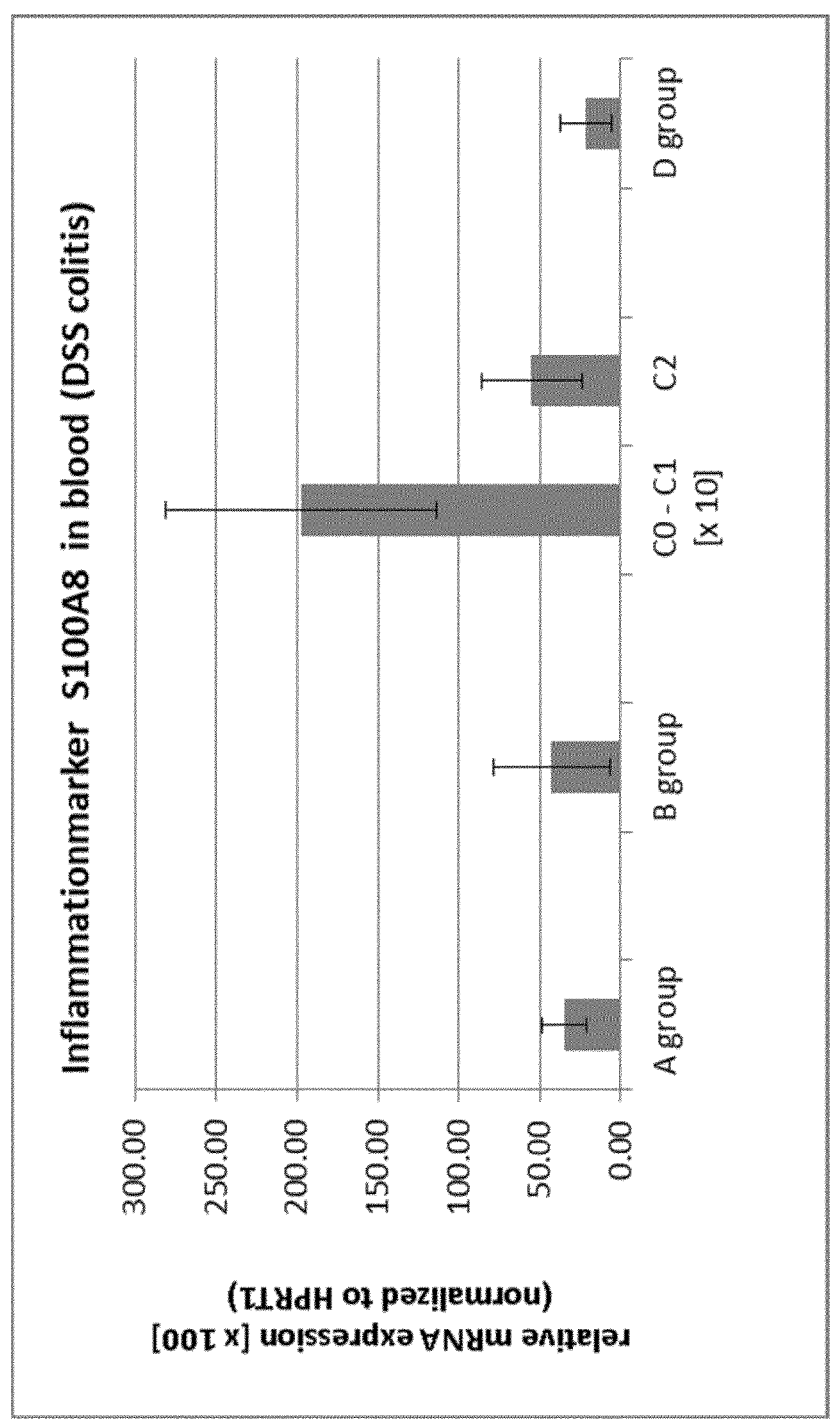

FIG. 4E: The expression of the "inflammation marker" S100A8 (calprotectin) in blood samples. "A group": No DSS in the drinking water for the whole experiment, "B group": DSS application until day 4, "B group": DSS application until day 8, development of severe colitis, "D group": 15 days recovery.

Figure 5A:
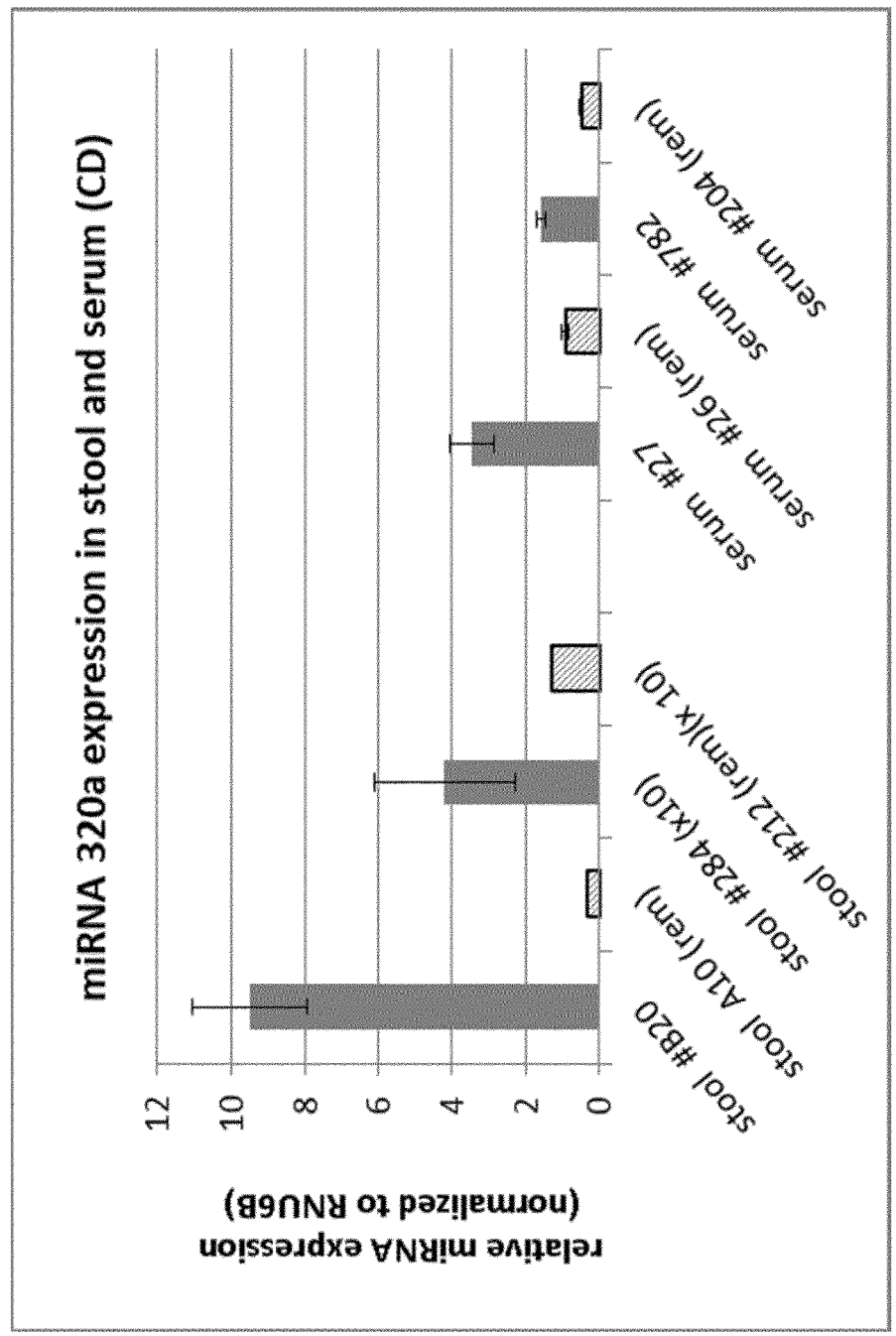
Figure 5B:
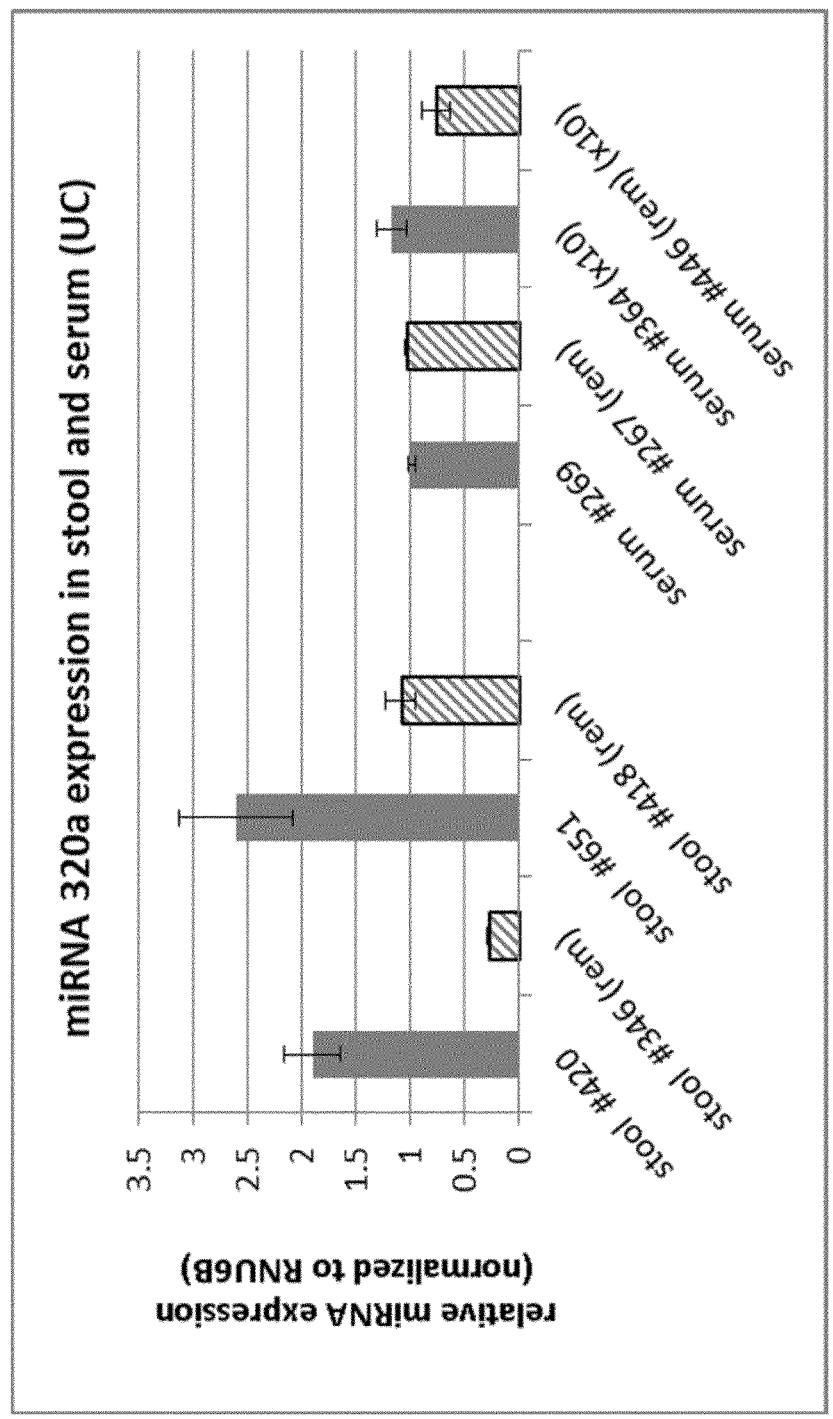

FIG. 5A+B: MicroRNA Expression analysis from stool and serum samples from human patients during Crohn's Disease (CD) and Ulcerative Colitis (CD).

Figure 5C:
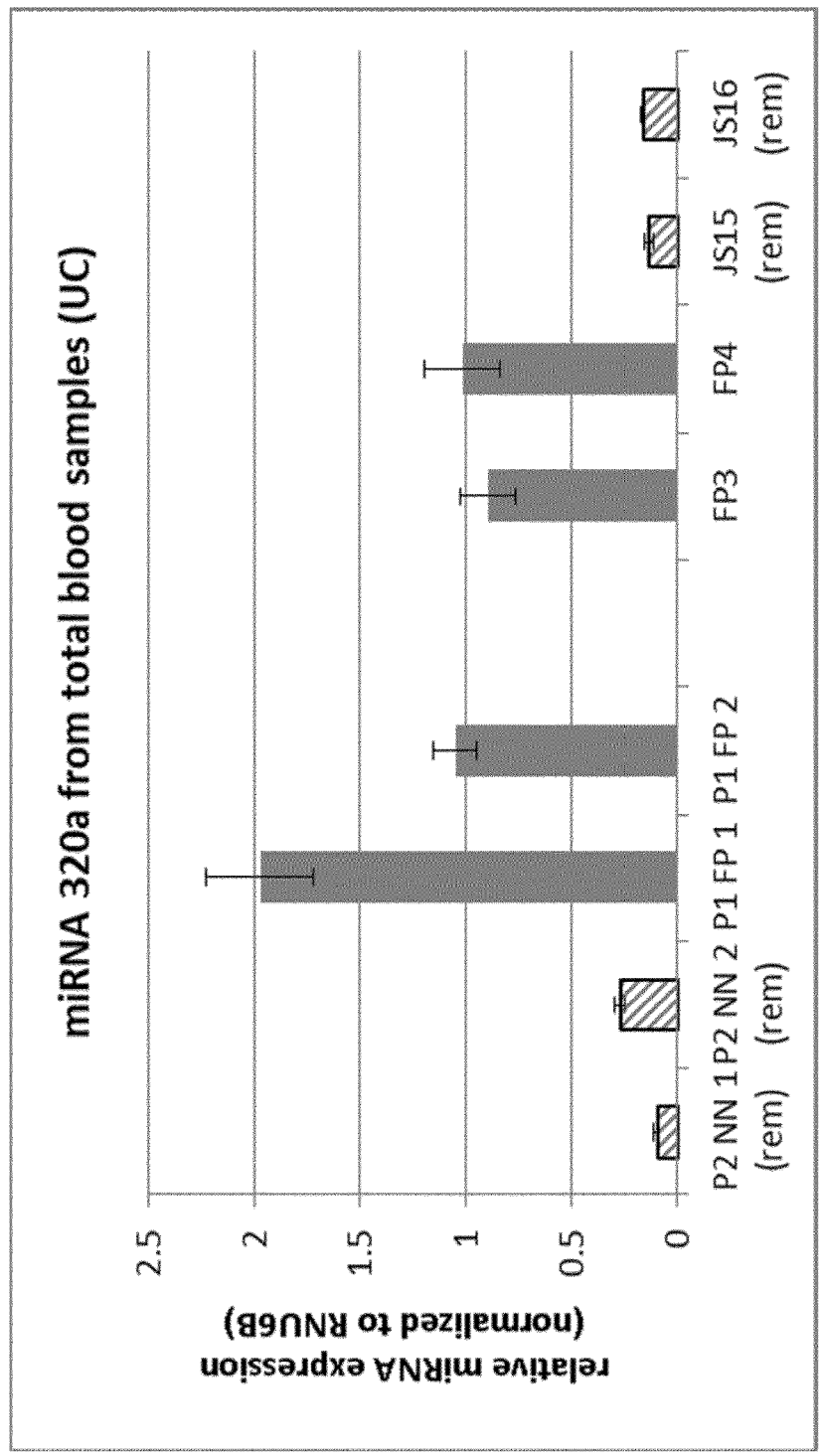

FIG. 5C: MiRNA expression in actual total blood samples (2012) from patients in remission (rem) and flare.

Figure 6A:
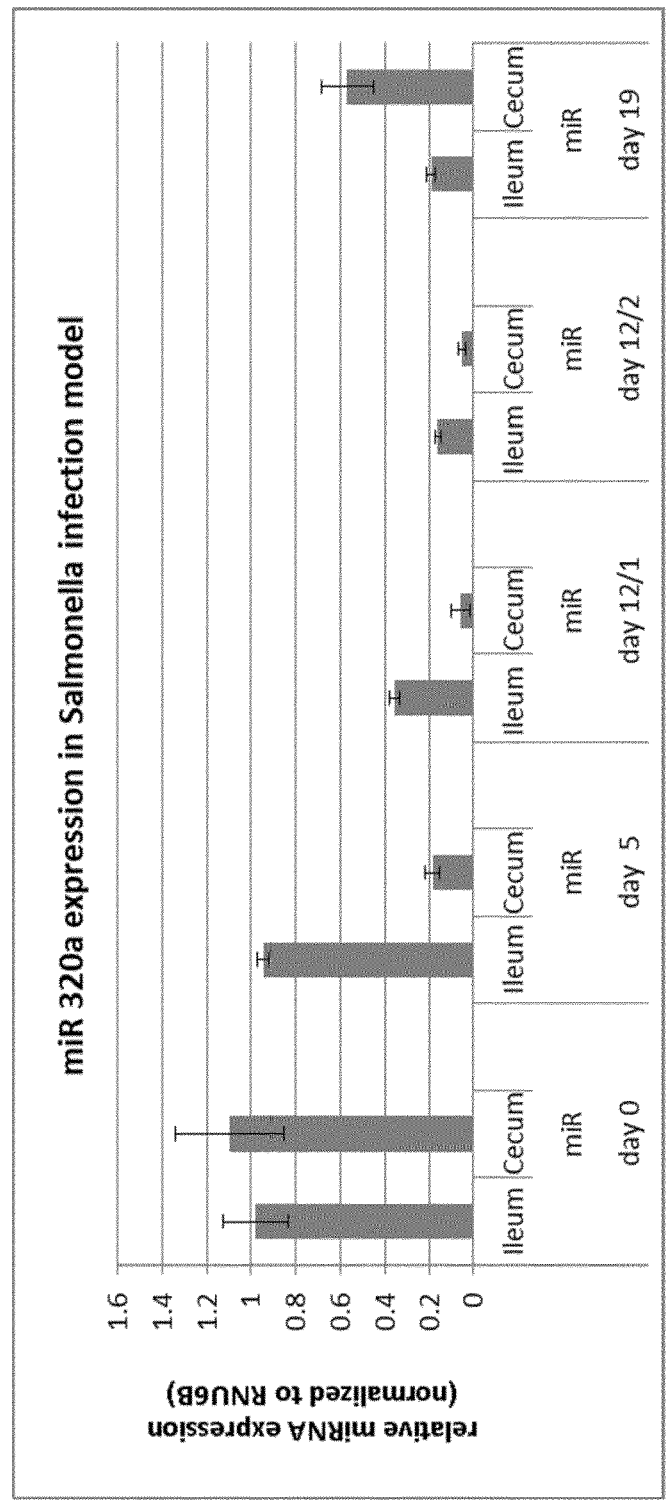
Figure 6B:
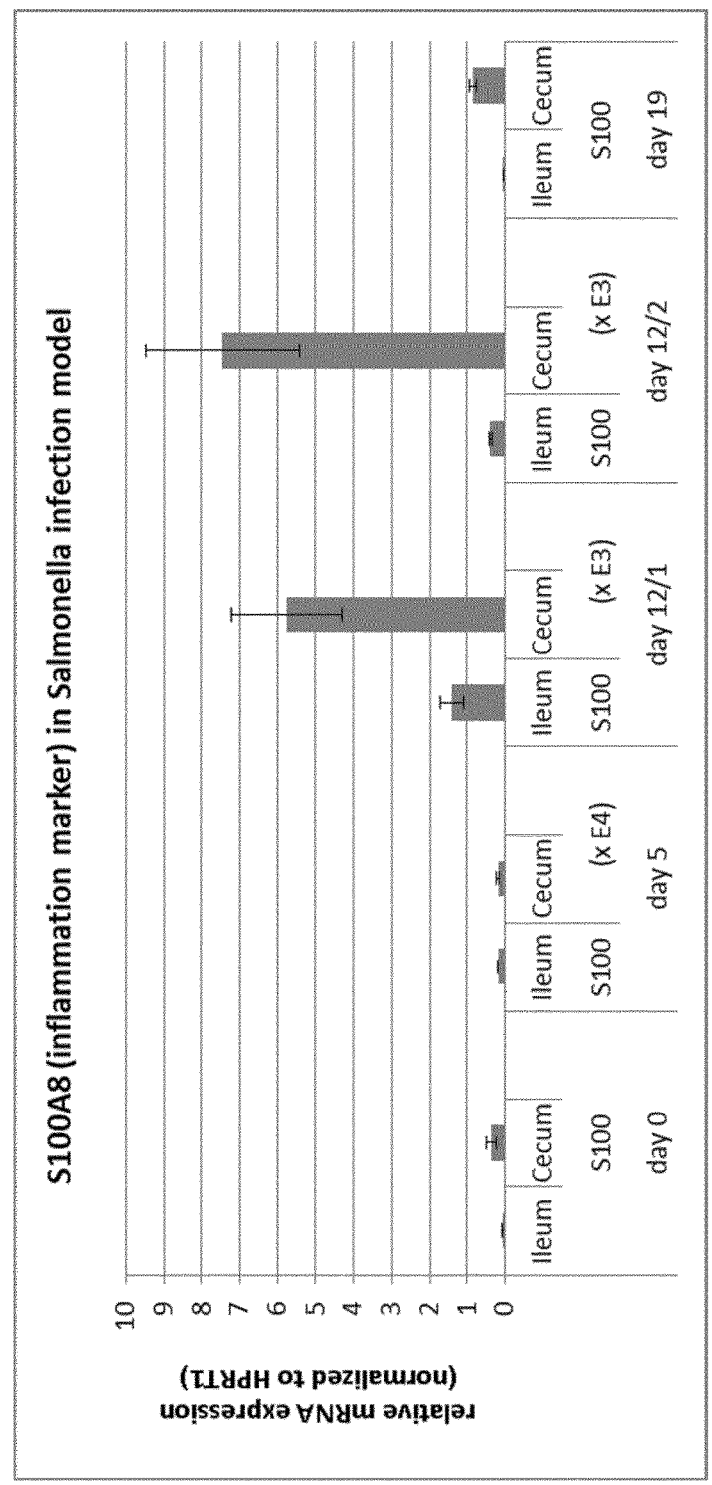

FIGS. 6A and B: Mir-320a does not show any increase during the time course of disease in a *Salmonella* infection model but the inflammation marker S100A8 reflects the inflammatory response in the mouse gut. (xE)=indicated value multiplied by ten to the power of.

DETAILED DESCRIPTION

The present invention relates to an in vitro method for diagnosing an acute or relapsing phase of inflammatory bowel disease in a subject, the method comprising
  i) determining the level of a nucleic acid molecule comprising any one of SEQ ID NO: 1 or 2 in a test sample;
  ii) comparing the level of the nucleic acid molecule determined in the test sample with a control sample;
    wherein an elevation of said nucleic acid molecule in the test sample is indicative of an acute or relapsing phase of said inflammatory bowel disease.

The present invention also relates to an in vitro method for diagnosing an acute or relapsing phase of inflammatory bowel disease in a subject, the method comprising
  i) determining the level of a nucleic acid molecule comprising any one of SEQ ID NO: 1 or 2 in a test sample;
  ii) comparing the level of the nucleic acid molecule determined in the test sample with a control sample;
    wherein an elevation of said nucleic acid molecule in the test sample in comparison to said control sample is indicative of an acute or relapsing phase of said inflammatory bowel disease.

The term "inflammatory bowel disease" or "IBD" as used herein is a collective term describing inflammatory disorders of the gastrointestinal tract, the most common forms of which are ulcerative colitis and Crohn's disease. The present invention provides methods for diagnosing and treating IBD of any etiology, preferably Crohn's disease (CD) and ulcerative colitis (UC). In certain embodiments, the present invention provides methods for diagnosing and treating ulcerative colitis, Crohn's disease, diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behcet's disease, gastroduodenal CD, jejunoileitis, ileitis, ileocolitis, Crohn's (granulomatous) colitis, irritable bowel syndrome, mucositis, radiation induced enteritis, short bowel syndrome, stomach ulcers, diverticulitis, pouchitis, proctitis, and chronic diarrhea. Reference to IBD throughout the specification is sometimes referred to in the specification as exemplary of gastrointestinal inflammatory conditions, and is not meant to be limiting. In certain embodiments, the present invention provides methods for diagnosing and/or treating ulcerative colitis and Crohn's disease. In certain embodiments, the present invention provides methods for diagnosing and/or treating ulcerative colitis. In certain embodiments, the present invention provides methods for diagnosing and/or treating Crohn's disease.

The term "acute phase of inflammatory bowel disease" as referred to herein means the first flare of a disease (see also FIG. 1A). In an acute phase, the disease is active and inflammatory markers are detectable. For example a certain threshold of inflammation may be needed to be crossed to give a detectable result (see FIG. 1A). For example, some inflammatory markers can only detectable when the acute phase is at its maximum.

On the other hand a "relapsing phase of inflammatory bowel disease" as referred to herein means the flares following the first flare of a disease. A "relapsing phase of inflammatory bowel disease" or "relapse" means that an acute phase of IBD is taking place after the first acute phase of IBD has occurred. A subject can experience many relapses throughout time (see also FIG. 1A). A relapse is determined in the same or similar way as outlined for the acute phase and vice versa. In a relapsing phase, the disease is active and inflammatory markers are detectable. Again, at which exact time point of a remission phase these markers are detectable depends on the marker used.

Both, an acute and a relapsing phase refer to disease flares. A "flare" can be determined using clinical disease activity indices, endoscopic indices, serum markers, faecal markers and other tests. Clinical indices, although they can be very in different in distinct IBD diseases, may present with any of the following symptoms: abdominal pain, vomiting, diarrhea, rectal bleeding severe internal cramps, muscle spasms in the region of the pelvis, weight loss. The most prevalent extraintestinal complication of inflammatory bowel disease is anemia.

However, these are indirect measurements of disease activity and may not accurately predict inflammatory activity found by e.g. endoscopic and histological examination. Diagnosis of an acute phase or relapsing phase of IBD is generally assessed by inflammatory markers in stool followed by colonoscopy with biopsy of pathological lesions. For example, markers such as e.g. ESR, C-reactive protein, $o_1$-acid glycoprotein (orosomucoid), thrombopoietin, platelet count, fibrinogen, lactoferrin, serum amyloid A, $o_1$-antitrypsin may be used, preferably S100A8 is used. Other markers are also known to the skilled artesian and e.g. summarized in Desai (2007) (Desai, Fabion and Sandborn (2007) Review article: biological activity markers in inflammatory bowel disease. *Aliment Pharmacol Ther* 25, 247-255).

Normally, acute phase or relapsing phase proteins are called proteins propagated as part of the innate immune response to occur in the context of tissue damage (e.g. inflammation or tissue damage in the case of IBD) within 6-48 hours in blood. Depending on the cause and course of their concentration increases. Further examples include C-reactive protein (CRP), Fibrinogen, Alpha1-antitrypsin, Alpha-antichymotrypsin, Serum amyloid A (SAA), Acid, alpha-1 glycoprotein haptoglobin, ceruloplasmin C3 and MBL complement, plasminogen, procalcitonin, Ferritin hepcidin, factor VIII, vWF, thrombopoietin.

Also there exist "negative acute phase proteins" also referred to as "antagonists" which show decreasing serum concentrations in acute inflammation. They include, inter alia albumin, antithrombin, transferrin, ransthyretin (prealbumin), retinol-binding proteins.

For example, to divide the Crohn's disease (CD) in active and remission stages or to measure flares of CD, one can e.g. use the Crohn's Disease activity index (CDAI) according to Best. Is the CDAI>150 there is an acute need of treatment boost. This equation is numerically simplified and utilizes eight selected variables, which is the Crohn's Disease Activity Index. Index values of 150 and below are associated with quiescent disease; values above that indicate active disease, and values above 450 are seen with extremely severe disease (Best et al., (1976) Development of a Crohn's disease activity index. National Cooperative Crohn's Disease Study. Gastroenterology 70(3):439-44). Most major research studies on medications in Crohn's disease define a response as a fall of the CDAI of greater than 70 points.

Similar disease activity stages are also described e.g. for ulcerative colitis (also named Colitis ulcerosa) as reviewed e.g. in Rizello et al. (Rizello et al. (2002) Review article: monitoring activity in ulcerative colitis. Aliment Pharmacol Ther 2002; 16 (Suppl. 4): 3-6).

For example for ucleratice colitis Truelove and Witts clinical criteria define a severe relapse as being characterized by more than six bloody stools daily and one or more of the following:

Temperature>37.8° C.,
pulse rate>90/min,
haemoglobin<10.5 g/dL or erythrocyte sedimentation rate>30 mm/h (Truelove and Witts (1954) Cortisone in ulcerative colitis: preliminary report on a therapeutic trial. Br Med J; 2: 375-8; Truelove and Jewell (1974) Intensive intravenous regimen for severe attacks of ulcerative colitis. Lancet; i: 1067-70).

Both, an acute phase and a relapse (or relapsing phase) of IBD can be accompanied with an elevation of S100A8 mRNA and/or protein expression in the blood of a subject in comparison with a control sample in accordance with the present invention. "S100A8" when used herein relates to the EF-hand proteins S100A8, which is important calcium signalling proteins that are involved in wound healing and provides a clinically relevant marker of inflammatory processes, such as inflammatory bowel disease. However, S100A8 can form homodimers via distinct modes of association, whereas in the presence of calcium S100A8 associates with S100A9 to form calprotectin, the physiologically active heterooligomer. Therefore, it is evident to the skilled artesian, that instead of measuring S100A8 similarly the level of S100A9 e.g. protein or mRNA also calprotectin or S100A9 may be used in the same manner giving the same results as obtained with the measurement of S100A8. It is also envisioned that wherever the level of the S100A8 mRNA is measured, alternatively also the protein level or the level of S100A9 or calprotectin may be analysed.

So, an increase in S100A8 mRNA and/or protein expression in a test sample in comparison to a control sample is an unspecific indication of an acute and/or relapsing phase of IBD. It can also be an unspecific marker for inflammation. However, S100A8 is a marker for an acute (or relapsing) inflammation, rather than being a marker specific for IBD (see FIG. 1A). Usually after a positive result for S100A8, and similarly for S100A9 and/or calprotectin, a doctor would then also use other techniques such as endoscopic examination to confirm the presence of IBD.

The "normal" level expression of a marker, when referred to herein, is the level of expression of the marker in a healthy subject e.g. a human patient not afflicted with an inflammatory bowel disease. Also envisaged as normal expression of a marker are data obtained from control samples. Thus, the control sample can be obtained from a healthy subject e.g. a subject, such as a human subject, not afflicted with an inflammatory bowel disease. Equally, a control subject can be a healthy subject e.g. a subject, such as a human subject, not afflicted with an inflammatory bowel disease.

An "elevated" or "increased" expression/level, "upregulated" or "over-expression" of a marker refers to an expression level in a test sample that is greater than the normal level of expression or a control value, and is preferably at least 1.5, more preferably 2, and 3, 4, 5, 6, 7, 8, 9, 10, 15, 20, 25, 30, 40, 50 times or more higher than the expression activity/level of the marker of the control sample (e.g. a sample from a healthy subject not expressing the marker associated with IBD) preferably, the average expression level of the marker in several control samples or the normal level of expression of the marker. In some embodiments, the expression level in a test sample that is elevated compared to the normal level of expression is at least 2 times higher than the expression level of the marker of the control sample. In some embodiments, the expression level in a test sample that is elevated compared to the normal level of expression is at least 3 times higher than the expression level of the marker of the control sample. In some embodiments, the expression level in a test sample that is elevated compared to the normal level of expression is at least 4 times higher than the expression level of the marker of the control sample. In some embodiments, the expression level in a test sample that is elevated compared to the normal level of expression is at least 6 times higher than the expression level of the marker of the control sample. In some embodiments, the expression level in a test sample that is elevated compared to the normal level of expression is at least 8 times higher than the expression level of the marker of the control sample.

It is envisaged by the present invention that the increased level of the nucleic acid molecule of SEQ ID NO: 1 or 2 or S100A8 mRNA is expressed as a "X-fold" of that nucleic acid sequence. Thus, a "fold change" means a measure describing how much a quantity changes going from an initial (control value or control sample) to a final value (test sample). For example, an initial value of 30 and a final value of 60 corresponds to a fold change of 2, or in common terms, a two-fold increase. Fold change is calculated as the ratio of the final value to the initial value i.e. if the initial value is A and final value is B, the fold change is B/A.

In one embodiment of the method of the present invention the X-fold for the nucleic acid molecule of SEQ ID NO: 1 or 2 is 2 for the test sample and the X-fold of the control or control sample is 0,5, here the fold change is 4.

In another embodiment of the method of the present invention the X-fold the nucleic acid molecule of SEQ ID NO: 1 or 2 is 30 for the test sample and the X-fold of the control or control sample is 5, here the fold change is 6.

In another embodiment of the method of the present invention the X-fold the nucleic acid molecule of SEQ ID NO: 1 or 2 is 2 for the test sample and the X-fold of the control or control sample is 0,25 here the fold change is 8.

Equally, thus the fold change of the nucleic acid molecule of SEQ ID NO: 1 or 2 in the test sample can be 2, 3, 4, 5, 6, 7, 8, 9, 10, 11, 12, 13, 14, 15, 16, 17, or higher. In one embodiment, the fold change is equal to or higher than 4. In another embodiment, the fold change is equal to or higher than 6. In another embodiment, the fold change is equal to or higher than 8.

A "down-regulated" expression of a marker refers to an expression level in the test sample that is similar or equal to the expression level of the marker in the control sample (e.g., sample from a healthy subject not having IBD or a patient having IBD, being in a remission phase) and preferably the average expression level of the marker in several control samples or the normal level of expression of the marker. However, this marker can be elevated before it becomes downregulated. Therefore, this term also describes a marker, which is up-regulated at a certain time point and goes back to the normal expression afterwards. Equally, however, a down-regulation may also refer to a marker which is expressed to a lesser extend as the expression level of the marker in the control sample (e.g., sample from a healthy subject not having IBD or a patient having IBD, being in a remission phase) and preferably the average expression level of the marker in several control samples or the normal level of expression of the marker.

The term "expression" when used herein can refer to the level of expression of a protein, mRNA and/or miRNA, meaning the amount present of these molecules in a sample.

A "marker" can be any marker, preferably a marker of inflammation, most preferably S100A8 protein and/or mRNA. In some embodiments of the present invention 1, 2, 3, 4, 5, 6, 7, 8, 9, 10 or more markers are analyzed at the same time or at different time points. The marker also includes nucleic acid molecules such as a nucleic acid molecule of SEQ ID NO: 1 and 2. Thus, the marker may be a protein, miRNA, mRNA. Also included are cells expressing such marker. A marker can be measured in biopsis, stool, urine, or blood samples, preferably stool and/or blood.

Accordingly, also the nucleic acid molecule of SEQ ID NO: 1 or 2 can be measured e.g. in biopsis stool, or blood samples, preferably stool or blood samples e.g. by RT-PCR. The nucleic acid molecule of SEQ ID NO: 1 or 2 is up-regulated in the blood probe before the up-regulation of S100A8 mRNA is evident in the blood (see also example 4, FIG. 4D, E). In one embodiment, the nucleic acid molecule of SEQ ID NO: 1 or 2 is measured in a stool sample. In another embodiment, the nucleic acid molecule of SEQ ID NO: 1 or 2 is measured in a blood sample. In another embodiment, the nucleic acid molecule of SEQ ID NO: 1 or 2 is measured in a serum sample.

The term "blood", "total blood" or "whole blood" is a bodily fluid in animals that delivers necessary substances such as nutrients and oxygen to the cells and transports metabolic waste products away from those same cells. In vertebrates, it is composed of blood cells suspended in blood plasma. "Plasma" constitutes 55% of blood fluid, is mostly water (92% by volume) as well as clotting factors. In a blood sample for example, plasma and blood cells, mainly red blood cells (also called RBCs or erythrocytes) and white blood cells, including leukocytes and platelets (thrombocytes) are present. Thus, in one embodiment, blood (whole blood) includes blood cells such as red blood cells, leukocytes and thrombocytes. In blood, the "serum" is the component that is neither a blood cell (serum does not contain white or red blood cells) nor a clotting factor; it is the blood plasma with the fibrinogens removed. In some embodiments, the blood sample is a serum sample. In other embodiments, the test sample is a (whole) blood sample. In other embodiments, the control sample is a whole blood sample.

In one embodiment of the method of the present invention, the elevation of said nucleic acid molecule in the test sample, which is stool, in comparison to said control sample or control value, is indicative of an acute or relapsing phase of said inflammatory bowel disease, preferably Crohn's disease (CD) and ulcerative colitis (UC), most preferably CD.

In one embodiment of the method of the present invention, the elevation of said nucleic acid molecule in the test sample, which is blood, in comparison to said control sample or control value, is indicative of an acute or relapsing phase of said inflammatory bowel disease, preferably Crohn's disease (CD) and ulcerative colitis (UC), most preferably UC.

In one embodiment of the method of the present invention, the elevation of said nucleic acid molecule in the test sample, which is serum, in comparison to said control sample or control value, is indicative of an acute or relapsing phase of said inflammatory bowel disease, preferably Crohn's disease (CD).

Similarly to the nucleic acid molecules of the present invention, also S100A8 protein and/or mRNA can also be measured in different test samples e.g. in biopsis stool, or blood samples, preferably stool or blood and/or serum samples of a subject e.g. by RT-PCR or by immunohistochemistry, respectively. In one embodiment, S100A8 protein and/or mRNA is measured in a stool sample. In another embodiment, the S100A8 protein and/or mRNA is measured in a blood sample. In another embodiment, the S100A8 protein and/or mRNA is measured in a serum sample. In another embodiment, the S100A8 protein and/or mRNA is measured in a whole blood sample. Preferably, S100A8 mRNA is measured. Again, likewise or instead of S100A8 also the level of S100A9 or calprotectin may be measured.

The term "remission" or "remission phase" refers to the temporary or permanent weakening of the symptoms of chronic disease, which can be achieved without a cure ("restitutio ad integrum"). A distinction is made between complete and partial remission. For example, remission of Crohn's disease is defined as CDAI below 150. A remission in UC may be determined by a method as described in Travis et al., (2011) (Review article: defining remission in ulcerative colitis. Aliment Pharmacol Ther. July; 34(2):113-24). In a remission phase the expression of the nucleic acid molecule of SEQ ID NO: 1 or 2 as well as the S100A8 mRNA are down-regulated again such that a normal expression or a nearby normal expression is again reached. As long as there is no other inflammation present, also markers of inflammation such as S100A8 should be down-regulated in a remission phase.

The present invention includes the measurement of nucleic acid molecules. As such a "nucleic acid molecule" when used herein encompasses any nucleic acid molecule having a nucleotide sequence of bases comprising purine and pyrimidine bases which are comprised by said nucleic acid molecule, whereby said bases represent the primary structure of a nucleic acid molecule. Nucleic acid sequences include DNA, cDNA, genomic DNA, RNA or synthetic forms, for example, PNA, and mixed polymers, both sense and antisense strands, or may contain non-natural or derivatized nucleotide bases, as will be readily appreciated by those skilled in the art. The polynucleotide of the present invention is preferably composed of any polyribonucleotide or polydeoxyribonucleotide, which may be unmodified RNA or DNA or modified RNA or DNA. For example, the polynucleotide can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. The polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, the term "nucleic acid molecules" embraces chemically, enzymatically, or metabolically modified forms. Preferably, the nucleic acid molecule of the present invention is RNA. In one embodiment, the nucleic acid molecule has the SEQ ID NO: 1 or 2. In another embodiment, the nucleic acid molecule has the SEQ ID NO: 1.

The term "RNA" includes any type of RNA such as e.g. mRNA, miRNA, siRNA, shRNA preferably miRNA and mRNA. In one embodiment, the RNA is a miRNA. In another embodiment, the RNA is a mRNA.

The sequences of SEQ ID NO: 1 is equivalent to a mature microRNA (miRNA) which can be found in the respective databases (for example www.mirbase.org) under the following non-limiting denominations: hsa-miR-320a (Accession number MIMAT0000510), ptr-miR-320a, ppy-miR-320a, bta-miR-320, cfa-miR-320, mmu-miR-320, rno-miR-320, and/or mml-miR-320. The species of origin is thereby designated with a three-letter prefix, e.g., hsa-miR-320a would be from human (Homo sapiens) and mmu-miR-320a would be a mouse (Mus musculus) miRNA. The sequences of SEQ ID NO: 2 is equivalent to the mature miRNA with the non-limiting denomination: ssc-miR-320. Other mature miRNAs might come up in the future and all these miRNAs are also within the scope of the present invention, provided that they consist of the sequence AAAAGCUGGGUUGA-GAGGGCGA SEQ ID NO: 1 and/or AAAAGCUGGGUUGAGAGGGCGAA SEQ ID NO: 2. It follows that the sequence AAAAGCUGGGUUGA-GAGGGCGA SEQ ID NO: 1 and/or AAAAGCUGGGUUGAGAGGGCGAA SEQ ID NO: 2 as used herein can be replaced with any miRNA sequence selected from the group consisting of hsa-miR-320a, ptr-miR-320a, ppy-miR-320a, bta-miR-320, cfa-miR-320, mmu-miR-320, rno-miR-320, and/or mml-miR-320 and/or ssc-miR-320 (or future miRNAs from other species or from different places in the genome) (see also table 1 for some miRNAs having the SEQ ID NO: 1 or SEQ ID NO: 2).

It will be understood, however, that irrespective of the nomenclature of the miRNAs, the present invention encompasses the detection of all nucleic acid sequences which consist of the isolated sequence AAAAGCUGGGUUGA-GAGGGCGA SEQ ID NO: 1 and/or AAAAGCUGGGUUGAGAGGGCGAA SEQ ID NO: 2 (either synthetically manufactured or naturally processed) and any precursors of said sequence, provided that the precursor leads to the expression or provision of the isolated sequence AAAAGCUGGGUUGAGAGGGCGA SEQ ID NO: 1 and/or AAAAGCUGGGUUGAGAGGGCGAA SEQ ID NO: 2 intracellularily, preferably in a host cell, preferably a eucaryotic cell, more preferably in a mammalian cell and most preferred in a human cell. miRNA genes are usually transcribed by RNA polymerase II. The product, which is called primary miRNA (pri-miRNA), may be hundreds or thousands of nucleotides in length and typically contains one or more miRNA stem loops. It is presently accepted that Pasha, also known as DGCR8 is required for micro RNA processing. It binds to Drosha, an RNase III enzyme, to form a Microprocessor complex that cleaves the pri-miRNA to the characteristic stem-loop structure of the pre-miRNA, which is then further processed to miRNA fragments by the enzyme Dicer and subsequently incorporated into the RNA-induced silencing complex (RISC). The pre-miRNA is frequently characterized by a two-nucleotide overhang at its 3' end and 3' hydroxyl and 5' phosphate groups.

The "precursors" of the nucleotide sequence of SEQ ID NO: 1 or 2 thus include pri-miRNAs and pre-miRNAs which upon processing in a cell (preferably a mammalian cell and more preferably in a human cell) lead to the mature miRNA nucleic acid sequence AAAAGCUGGGUUGA-GAGGGCGA SEQ ID NO: 1 or AAAAGCUGGGUUGA-GAGGGCGAA SEQ ID NO: 2.

Means and methods to test whether a given precursor is processable to the sequence AAAAGCUGGGUUGAGAGGGCGA SEQ ID NO: 1 or AAAAGCUGGGUUGAGAGGGCGAA SEQ ID NO: 2 are within the means and expertise of the skilled person. To this end it is for example possible to specifically capture the processed target sequence AAAAGCUGGGUUGAGAGGGCGA SEQ ID NO: 1 and/or AAAAGCUGGGUUGAGAGGGCGAA SEQ ID NO: 2 and/or to amplify the respective sequence by means of standard PCR-amplification techniques, and thereby to evaluate whether a precursor is indeed processable to said target sequence or not. Commercially available assays may be used in this regard, which assays are meanwhile offered by many companies including QIAGEN.

"Processable precursors" as disclosed herein, thus include natural precursor molecules which are processed intracellularly by either all or a selection of the respective miRNA processing steps, and which result in the desired miRNAs (equivalent to the sequence AAAAGCUGGGUUGAGAGGGCGA SEQ ID NO: 1 or AAAAGCUGGGUUGAGAGGGCGAA SEQ ID NO: 2)—these non-limiting miRNA processing steps may include inter alia: transcription of miRNA genes by RNA polymerase II; processing by Pasha/DGCR8 and Drosha, an RNase III enzyme, to form a Microprocessor complex that cleaves the pri-miRNA to the characteristic stem-loop structure of the pre-miRNA, which is then further processed to miRNA fragments by the enzyme Dicer and subsequently incorporated into the RNA-induced silencing complex (RISC).

A processable precursor is preferably characterized by one or more of the following structural and functional characteristics:
(a) the precursor is capable of forming a stem-loop (a double helix that ends in an unpaired loop —it occurs when two regions of the same strand, usually at least in part complementary in nucleotide sequence when read in opposite directions, base-pair to form a double helix that ends in an unpaired loop);
(b) the precursor is processable (cleavable) by Dicer;
(c) the precursor is at least in part double stranded;
(d) the precursor contains a part (third part) which is identical to the mature miRNA (equivalent to the sequence AAAAGCUGGGUUGAGAGGGCGA SEQ ID NO: 1 or AAAAGCUGGGUUGAGAGGGCGAA SEQ ID NO: 2) and a further part (first part) which is at least partially complementary thereto;
(e) the third part and the first part (see (d)) are spaced apart by a second part;
(f) at least the first and the third part of the precursor (see (d)) are made out of nucleotides;
(g) some or all of said nucleotides mentioned in (f) can be modified (such modifications include for example those that are detailed in WO 2006/137941 and/or
(i) the precursor can be transported across the nucleolemma by a karyopherin, preferably by Exportin-5.

Precursors which are characterized by at least the above mentioned characteristic (c) or (d) are preferred. Precursors which are characterized by at least the above mentioned characteristic (d) and (c) are more preferred. Precursors which are characterized by at least the above mentioned characteristic (d) and (c) and (f) are even more preferred.

"Processable" thus means in essence that all the precursors mentioned herein can be processed intracellularily to the isolated sequence AAAAGCUGGGUUGA-GAGGGCGA SEQ ID NO: 1 and/or AAAAGCUGGGUUGAGAGGGCGAA SEQ ID NO: 2. As mentioned before, said nucleic acid molecule is preferably processable by a mammalian cell and most preferred by a human cell.

It is envisaged that, within the context of all embodiments of the present invention, one or more or even all of the nucleotide(s) "U" of the sequence AAAAGCUGGGUUGA-GAGGGCGA SEQ ID NO: 1 or AAAAGCUGGGUUGA-GAGGGCGAA SEQ ID NO: 2 (or any other sequence disclosed herein) can be replaced by the nucleotide "T".

The present invention also relates to diagnosing IBD. The term "diagnosing" refers to both the process of attempting to determine or identify a possible disease or disorder and to the opinion reached by this process. Biological markers of disease activity have been studied in inflammatory bowel disease (IBD) as indicators of disease severity or activity and to predict the risk of relapse in patients in remission. Diagnosing of IBD typically is performed in a subject. The "subject" typically includes mammals, and in particular human beings, cats, dogs, camels, horses, sheep, cows, apes, pigs, guinea pigs, goats etc., human beings being preferred.

Within the present invention, the level of a nucleic acid molecule of the present invention and/or S100A8, S100A9, calrotectin is measured or determined. "Determining the level of a nucleic acid molecule", means the detection of a nucleic acid molecule such as SEQ ID NO: 1 or 2 in a sample, preferably the test sample. The level can be the presence or absence of the nucleic acid molecule in the test sample, but can also be the amount of expression of the nucleic acid molecule in said test sample. The amount of expression of the nucleic acid molecule can be obtained by standard procedures known to the person skilled in the art. Preferably, the level of said nucleic acid molecule is determined by qRT-PCR. In one embodiment, the level of the nucleic acid molecule of SEQ ID NO: 1 or 2 is analyzed in comparison to the level of said nucleic acid molecule of SEQ ID NO: 1 or 2 in a control sample or a control value. An "elevation" of said nucleic acid molecule and/or S100A8, S100A9 or calprotectin means for example an increase in the value such as the total expression, which can be measured by standard techniques such as RT-PCR. It can also mean the mere presence of the nucleic acid molecule in a test sample, in comparison to an absence or lower value/expression of said nucleic acid molecule in the control sample. In one embodiment, the nucleic acid molecule of SEQ ID NO: 1 or 2 determined in the test sample is elevated compared to a control sample or a control value and/or a certain cut-off value determined by the person skilled in the art. In another embodiment, the nucleic acid molecule of SEQ ID NO: 1 or 2 determined in the test sample is elevated compared to a control sample or a control value.

The values of the nucleic acid molecule of the present invention and/or the level of S100A8, S100A9, calrotectin can be measured/detected in a test sample and/or a control sample, or can also comprise a control value. In this regard a "test sample" means a sample reflecting the condition of a subject having IBD or being at risk of having IBD. Within the present invention, the test sample is a biological sample from a patient. A test sample further comprises any sample obtained not using endoscopy.

A test sample further comprises any sample obtained except for a sample primarily made out of tissue. The test sample can be selected from stool, urine, blood, salvia, preferably the test sample is a stool or a blood sample, most preferably a blood sample. The test sample can also be present within a subject. The test sample is also any sample other than biopsy.

On the other hand a "control sample" means any sample reflecting a condition of a healthy subject. Within the present invention, the control sample can be biological sample from a patient. The control sample can be selected from stool, urine, blood, salvia, preferably a blood sample, preferably obtained from a control subject. The control sample can also be present within a control subject. The control sample can be any sample other than biopsy. The control sample can also be a standard value. In some embodiments, the control sample is of the same type as the test sample. In some embodiments, the control sample is of a different type as the test sample. A control sample further comprises any sample obtained not using endoscopy.

Along this line, a "control" or "control value" for the purposes of the present invention comprises healthy (control) subjects, preferably subjects who do not have IBD or even standard controls that represent a healthy control group, or general, known in the art standards for IBD. Subjects of the control group ideally have no concurrent IBD. A control group is a group of several healthy to operators covers, for example, 3 or more, preferably 5 or more, more preferably 10 , 20, 30 , 40, or 50 persons health is examined with known methods, some of which are also mentioned in the introduction of the application on testing for IBD.

For the purposes of the present invention, the diagnosis can be based of ROC curves cut-off fixed values. ROC curves (Receiver-Operating—Characteristics) provide an overview of the diagnostic accuracy of a diagnostic test. Different cut-off values (possible also each measurement point) True positive rate (or sensitivity) and false-positive rate (1−specificity=) are plotted against each other. The determination of cut-off values is governed by the Consensus Paper No. CLSI C28-A2 the FDA. A so-determined cut-off value is then used as a reference value with which the amount/level of a nucleic acid molecule of any of SEQ ID NO: 1 or 2 can be compared.

The skilled artisan can also create cut-off values e.g. according to Singh (G Singh. *Determination of Cutoff Score for a Diagnostic Test*. The Internet Journal of Laboratory Medicine. 2006 Volume 2 Number 1). Targeted is a specificity, for example, 95% or 99%. Here the group of non-patients (or the group that corresponds to the test results negative such as e.g. healthy patients or patients in a remission phase) is calculated the corresponding percentile using the values (95% percentile 95th value at 100, according to size ordered values For N<>100 is interpolated accordingly). In MS—Excel the function "=PERCENTILE" (range of cells; 0.95) can be used—If possible, the confidence interval should be specified. This allows e.g. the software Medcalc. In the following article the calculation of the confidence interval is described using the binomial distribution (Campbell and Gardner (1988) Calculating Confidence Intervals for some non-parametric Analyses British Medical Journal, 296, 1454-1456).

According to the invention the skilled person can set the cut-off values for the nucleic acid molecule of SEQ ID NO: 1 or 2 and/or an additional marker of the present invention, e.g. S100A8 mRNA.

Furthermore, the results obtained from a test sample can be compared to the results obtained from a control sample and/or control value. Thus, the sentence "comparing the level of the nucleic acid molecule determined in the test sample with a control sample" means comparing the results obtained from determining the test sample with the results obtained from a control sample and/or control value. This can mean that the nucleic acid molecule of SEQ ID NO: 1 or 2 is present in the test sample, while it is absent in the control sample. It can also be that the nucleic acid molecule of SEQ ID NO: 1 or 2 is present in both, the test sample and the control sample, although the value can be lower in the control sample. It is thus envisaged that the level of the nucleic acid molecule of SEQ ID NO: 1 or 2 in the test sample is elevated when compared to the value of the control sample. However, the level of the nucleic acid molecule of SEQ ID NO: 1 or 2 in the test sample can be also equal, when compared to the value of the control sample. In one embodiment, the nucleic acid molecule of SEQ ID NO: 1 or 2 determined in the test sample is compared to a control sample or control value. In another embodiment, the nucleic acid molecule of SEQ ID NO: 1 or 2 determined in the test sample is compared to a control sample. In another embodiment, the nucleic acid molecule of SEQ ID NO: 1 or 2 determined in the test sample is compared to a control value.

Measuring of the level of the nucleic acid molecules of the present invention and/or the level of S100A8, S100A9 and/or calprotectin indicates the presence or absence of an acute or relapsing phase of said inflammatory bowel disease. The term "indicative of an acute or relapsing phase of said inflammatory bowel disease" means that an elevation of said nucleic acid molecule of SEQ ID NO: 1 or 2 in the test sample in comparison to the control sample or control value indicates that an acute or relapsing phase of IBD is present in said subject. Likewise, no change or a decrease of said nucleic acid molecule in the test sample in comparison to the control sample or control value indicates that an acute or relapsing phase of said IBD is absent. The elevation is measured by the level of said nucleic acid molecule present in the test sample and optionally comparing it to a control sample or control value. This can be done by any technique known in the art, preferably by RT-PCR.

In some embodiments, the method of the invention is an in vitro method for diagnosing an acute phase of inflammatory bowel disease in a subject.

In some embodiments, the method of the invention is an in vitro method for diagnosing a relapsing phase of inflammatory bowel disease in a subject.

In addition to the level of the nucleic acid molecules of the present invention also the "level of the S100A8" can be determined by standard procedures. It can mean the determination of the presence or absence of S100A8 mRNA or protein, preferably mRNA. It is also envisaged that the level of S100A8 mRNA or protein, preferably mRNA, is determined by techniques known to the person skilled in the art. Alternatively, also the level of S100A9 and/or Calprotectin (S100A8/S100A9-Heterotetramer) can be determined instead of S100A8. Therefore the embodiments/disclosure concerning S100A8 also apply mutatis mutandis to S100A9 or calprotectin.

In one embodiment, the level of S100A8 is analyzed with the same technique as the level of the nucleic acid molecule of any of SEQ ID NO: 1 or 2. Optionally, the level of S100A8 in the test sample is compared to the S100A8 level present in the control sample or a control value for S100A8.

In another embodiment, the level of S100A8 in the test sample is increased in an acute or relapsing phase of IBD when compared to the level of S100A8 present in the control sample. In another embodiment, the level of S100A8 in the test sample is unchanged in an acute or relapsing phase of IBD when compared to the level of S100A8 present in the control sample.

In a further embodiment of the method of the present invention, the method further comprises the step of determining the S100A8 mRNA level in said test sample and optionally comparing it to the level in the control sample. In another embodiment, the method of the present invention comprises the step of determining the S100A8 mRNA level in said test sample and optionally comparing it to the level in the control sample or control value. In a further embodiment, the method of the present invention comprises the step of determining the S100A8 protein level in said test sample and optionally the step of comparing it to the level in the control sample or control value.

In another embodiment in the method of the present invention, the level of S100A8 mRNA in said subject exhibits no alteration/no difference when compared to the control subject. Likewise, in another embodiment in the method of the present invention, the level of S100A8 mRNA in said test sample exhibits no alteration/no difference when compared to the control sample or control value.

In another embodiment in the method of the present invention, the level of S100A8 mRNA in said subject exhibits an elevation when compared to the control subject. Likewise, in another embodiment in the method of the present invention, the level of S100A8 mRNA in said test sample exhibits an elevation when compared to the control sample or control value.

There are different possibilities how the nucleic acid molecules of the present invention can be measured/detected. Likewise, for e.g. S100A8 the method of detection also depends on what is to be measured. For example, here either the mRNA but also the protein may be detected. In one embodiment, the level of S100A8 mRNA is determined by qRT-PCR. In another embodiment, the level of the nucleic acid molecule of SEQ ID NO: 1 or 2 is determined by qRT-PCR. In another embodiment, the level of the nucleic acid molecule of SEQ ID NO: 1 or 2 as well as the level of S100A8 mRNA is determined by qRT-PCR. The terms "RT-PCR", "qRT-PCR" and "quantitative RT-PCR" are known to the person skilled in the art. Reverse transcription polymerase chain reaction (RT-PCR) is one of many variants of polymerase chain reaction (PCR). This technique is commonly used in molecular biology to detect RNA expression levels Quantitative RT-PCR is used to quantify mRNA in both relative and absolute terms. It can be applied for the quantification of mRNA and/or miRNA expressed from endogenous genes, which may also include normalization to "standard" mRNA or miRNA (see also Bustin et al. (2005) Quantitative real-time RT-PCR—a perspective. J Mol Endocrinol Jun. 1, 2005 34 597-601, Peltier and Latham (2008 Normalization of microRNA expression levels in quantitative RT-PCR assays: Identification of suitable reference RNA targets in normal and cancerous human solid tissues. RNA. May 2008; 14(5): 844-852, Żyżyńska-Granica and Koziak (2012) Identification of Suitable Reference Genes for Real-Time PCR Analysis of Statin-Treated Human Umbilical Vein Endothelial Cells. PLoS One 7(12) and Bustin (2000) Absolute quantification of mRNA using real time reverse transcription polymerase chain reaction assays. Journal of Molecular Endocrinology 25, 167-193). RT-PCR is used to clone expressed genes by reverse transcribing the RNA of interest into its DNA complement through the use of reverse transcriptase. Subsequently, the newly synthesized cDNA is amplified using traditional PCR. In addition to qualitatively study gene expression, quantitative PCR can be utilized for quantification of RNA, in both relative and absolute terms by incorporating qPCR into the technique. The combined technique, described as quantitative RT-PCR.

A "quantitative detection" in connection with an RT-PCR is also known to the skilled artesian. There are two main methods used to perform quantitative RT-PCR: dye-based and probe-based detection. Both methods rely on calculating the initial (zero cycle) DNA (cDNA) concentration by extrapolating back from a reliable fluorescent signal. The basic principle of this method is known in the art (Arya et al. 2005 Expert Review of Molecular Diagnostics; Vol. 5, No. 2, Pages 209-219). The term "multiplex" refers to amplification with more than one set of primers. In some embodiments, the test sample and control sample are analyzed simultaneously in a multiplex qRT-PCR. In other embodiments, the test sample and control sample are analyzed singularly by qRT-PCR. In some embodiments, only the test sample is analyzed by qRT-PCR.

The quantification of mRNA and/or miRNA using RT-PCR can be achieved as either a one-step or a two-step reaction. The difference between the two approaches lies in the number of tubes used when performing the procedure. In the one-step approach, the entire reaction from cDNA synthesis to PCR amplification occurs in a single tube. On the other hand, the two-step reaction requires that the reverse transcriptase reaction and PCR amplification be performed in separate tubes. It is also the preferred method of analysis when using DNA binding dyes such as SYBR Green since the elimination of primer-dimers can be achieved through a simple change in the melting temperature.

In one embodiment, the method of the present invention comprises the steps of
a) extracting RNA from the test sample;
b) performing qRT-PCR with specific oligonucleotides suitable to detect the nucleic acid molecule of SEQ ID NO: 1 or 2.

Here, the "extracting" or "extraction" of RNA is the purification of RNA from biological samples. This procedure is complicated by the ubiquitous presence of ribonuclease enzymes in cells and tissues, which can rapidly degrade RNA. Several methods are used in molecular biology to isolate RNA from samples, one of these is Guanidiniumthiocyanate-phenol-chloroformextraction. In one embodiment, the RNA, preferably miRNA is extracted from the test sample. The method of the present invention can also include the extraction of RNA, preferably mRNA from a control sample.

Moreover, the term "oligonucleotide" as used herein refers to a nucleic acid that includes at least two nucleic acid monomer units (e.g., nucleotides). An oligonucleotide typically includes from 5 to 175 nucleic acid monomer units, more typically from eight to 100 nucleic acid monomer units, and still more typically from 10 to 50 nucleic acid monomer units (e.g., about 15, about 20, about 25, about 30, about 35, or more nucleic acid monomer units). The exact size of an oligonucleotide will depend on many factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (*Meth. Enzymol.* 68:90-99, 1979); the phosphodiester method of Brown et al. (*Meth. Enzymol.* 68:109-151, 1979); the diethylphosphoramidite method of Beaucage et al. (*Tetrahedron Lett.* 22:1859-1862, 1981); the triester method of Matteucci et al. (*Am. Chem. Soc.* 103:3185-3191, 1981); automated synthesis methods; or the solid support method of U.S. Pat. No. 4,458,066, or other methods known to those skilled in the art.

A "primer" as used herein refers to a oligonucleotide capable of acting as a point of initiation of template-directed nucleic acid synthesis when placed under conditions in which polynucleotide extension is initiated (e.g., under conditions comprising the presence of requisite nucleoside triphosphates (as dictated by the template that is copied) and a polymerase in an appropriate buffer and at a suitable temperature or cycle(s) of temperatures (e.g., as in a polymerase chain reaction). Primers can also be used in a variety of other oligonucleotide-mediated synthesis processes, including as initiators of de novo RNA synthesis and in vitro transcription-related processes (e.g., nucleic acid sequence-based amplification (NASBA), transcription mediated amplification (TMA), etc.). A primer is typically a single-stranded oligonucleotide (e.g., oligodeoxyribonucleotide). The appropriate length of a primer depends on the intended use of the primer but typically ranges from 6 to 40 nucleotides, more typically from 15 to 35 nucleotides. In one embodiment, the primer has 21 nucleotides. Short primer molecules generally require lower temperatures to form sufficiently stable hybrid complexes with the target sequence on a template than longer primers.

A primer can be labeled, if desired, by incorporating a label detectable by spectroscopic, photochemical, biochemical, immunochemical, or chemical means. For example, useful labels include $^{32}$P, fluorescent dyes, electron-dense reagents, enzymes (as commonly used in ELISA assays), biotin, or haptens and proteins for which antisera or monoclonal antibodies are available. In one embodiment, the primer is a Lux primer. In another embodiment, the primer is a scorpion primer. In another embodiment, the primer is radiolabelled. In one embodiment, the primer is a Lux primer, a scorpion primer or is radiolabelled.

In one embodiment, the oligonucleotides used in the method of the present invention are specific oligonucleotides suitable to detect any of the nucleic acid molecules shown in SEQ ID NO: 1 or 2. In another embodiment of the present invention the specific oligonucleotides are shown in SEQ ID NO: 4 and/or 5.

In another embodiment, the oligonucleotides used in the method of the present invention are specific oligonucleotides suitable to detect S100A8 mRNA. In another embodiment of the present invention the specific oligonucleotides are shown in SEQ ID NO: 3 and/or 4.

In another embodiment, the method of the present invention includes that the level of the nucleic acid molecule of SEQ ID NO: 1 or 2 is detected by a method comprising:
  a) extracting RNA from said test sample;
  b) treating the obtained RNA with a reverse transcription reaction mixture comprising specific oligonucleotides corresponding to the nucleic acid molecule of SEQ ID NO: 1 or 2, dNTPs and a reverse transcriptase under conditions allowing transcription of the nucleic acid molecule into complementary DNA (cDNA);
  c) quantitative detection of cDNA transcripts of said nucleic acid molecule,
wherein steps b) and c) can be either performed in separate reactions or in one reaction.

In one embodiment, the steps b) and c) are performed in separate reactions. In another embodiment, the steps b) and c) are performed in one reaction.

In a further embodiment, the method of the present invention can include that only specific nucleoside triphosphates are used. For example only dNTPs, ddNTPs or rNTPs may be present in the method. It can also be that 1, 2 or 3 different types of dNTPs are present in the method. It can also be that 1, 2 or 3 different types of rNTPs are present in the methods.

In one embodiment of the method of the present invention, the extracting step is omitted. The extraction can be omittable according to Shi and Liu (Shi and Liu (1992) Direct reverse transcription-polymerase chain reaction from whole blood without RNA extraction (Shi and Liu (1992) Genet Anal Tech Appl. 9(5-6):149-50).

In a further embodiment, said specific oligonucleotides are selected from a group consisting of SEQ ID NO: 3 and/or SEQ ID NO: 4. In a further embodiment, said specific oligonucleotides are selected from a group consisting of SEQ ID NO: 5 and/or SEQ ID NO: 6 (for the detection of SEQ ID NO: 1 or 2).

A "reverse transcription" as used herein means the process of the generation of complementary DNA (cDNA) from a RNA template usually mediated by an enzyme such as the reverse transcriptase. Well studied reverse transcriptases include: HIV-1 reverse transcriptase from human immunodeficiency virus type 1 (PDB 1HMV), M-MLV reverse transcriptase from the Moloney murine leukemia virus and the AMV reverse transcriptase from the avian myeloblastosis virus. For miRNA-specific reverse transcription there are different methods. In one approach, miRNAs are reverse transcribed individually by using stem-loop-specific reverse transcription primers that are designed to have a short single-stranded region that is complementary to the known sequence on the 3' end of the miRNA, a double-stranded part (the stem) and the loop that contains the universal primer-binding sequence. The resulting reverse transcription product (cDNA) is then used as a template for qPCR with 1 miRNA-specific primer and a second universal primer (TaqMan PCR, Applied Biosystems). Another approach first elongates the 3' ends of all miRNAs with a poly(A) tail using E coli poly(A) polymerase (miRCURY, Exiqon). A primer consisting of an oligo(dT) sequence with a universal primer-binding sequence at its 5' end is then used to prime reverse transcription and to amplify the target sequences in the qPCR reaction. The stretch of "dTs" between the miRNA and the universal sequence of the oligo(dT) primer is defined by using a template binding sequence at the 5' end of the primer that anchors the primer to the 3' end of the miRNA. This approach is especially useful if several different miRNAs need to be analyzed from a small amount of starting material (see van Rooij (2011) The Art of MicroRNA Research Circulation Research. 108: 219-234). Therefore the term "reverse transcription reaction mixture" means a mixture in which a reverse transcription can take place.

The present invention further relates to a method for treating the acute or relapsing phase of inflammatory bowel disease in a subject comprising:
  (a) determining the level of any of SEQ ID NO: 1 or 2 in a test sample;
  (b) comparing both levels to a control sample or control value; and
  (c) treating said subject with MEDICAMENT, provided that said test sample is characterized by an increase of said SEQ ID in comparison to said control sample or control value.

The present invention further relates to a method for diagnosing the acute phase and/or a relapsing phase of inflammatory bowel disease comprising:
  (a) determining the level of SEQ ID NO: 1 or 2 in a test sample;
  (b) determining the level of S100A8 mRNA in said test sample; and
  (c) comparing both levels to a control sample or control value;

wherein an increase of said SEQ ID and no alteration of said S100A8 in comparison to said control sample or control value indicates the acute and/or relapsing phase of inflammatory bowel disease.

The present invention further relates to a method for treating the acute or relapsing phase of inflammatory bowel disease in a subject comprising:
 (a) determining the level of any of SEQ ID NO: 1 or 2 in a test sample;
 (b) determining the level of S100A8 mRNA in said test sample;
 (c) comparing both levels to a control sample or control value; and
 (d) treating said subject with MEDICAMENT, provided that said test sample is characterized by an increase of said SEQ ID and by no alteration of said S100A8 in comparison to said control sample or control value.

In some embodiments, the methods for treating of the present invention are methods for treating an acute phase of inflammatory bowel disease. In some other embodiments, the methods for treating of the present invention are methods for treating a relapsing phase of inflammatory bowel disease.

The present invention further relates to a method for stopping treating the acute or relapsing phase of inflammatory bowel disease in a subject comprising:
 (a) determining the level of any of SEQ ID NO: 1 or 2 in a test sample;
 (b) comparing the levels to a control sample or control value; and
 (c) stopping treating said subject with MEDICAMENT, provided that said control sample is characterized by no difference of said SEQ ID in comparison to said control sample or control value.

The term "no difference" or "no alteration" as used herein, means no significant difference when compared to a control sample or control value. Of course, the values may have some errors or standard deviation e.g. due to small inevitable pipetting errors, when detecting the value of the SEQ IDs of the present invention or S100A8. No difference thus does not necessarily mean the very same values, but values being similar and/or within the range of normally observed standard deviations. Techniques to analyze these as for example in a method would be to perform technical or biological replicates in qRT-PCR for example. The biological replicates here also include several test samples of one subject. In some embodiments, the detection of no difference or no alteration can also be a downregulation. This is for example the case if said test sample is the second, third, fourth, fifth, sixth, seventh or more test sample obtained from the very same subject in the course of time.

In one embodiment of the method of the present invention, no difference of said nucleic acid molecule in the test sample, which is stool, in comparison to said control sample or control value, is indicative of a remission phase or the absence of an acute or relapsing phase said inflammatory bowel disease, preferably Crohn's disease (CD) and ulcerative colitis (UC).

In another embodiment of the method of the present invention, no difference of said nucleic acid molecule in the test sample, which is blood, in comparison to said control sample or control value, is indicative of a remission phase or the absence of an acute or relapsing phase said inflammatory bowel disease, preferably Crohn's disease (CD) and ulcerative colitis (UC).

In further embodiments of the method of the present invention, no difference of said nucleic acid molecule in the test sample, which is serum, in comparison to said control sample or control value, is indicative of a remission phase or the absence of an acute or relapsing phase said inflammatory bowel disease, preferably Crohn's disease (CD).

In another embodiment of the method of the present invention, no difference of said nucleic acid molecule in the test sample, which is blood, in comparison to said control sample or control value, is indicative of a remission phase or the absence of an acute or relapsing phase said inflammatory bowel disease, preferably ulcerative colitis (UC).

The present invention further relates to a MEDICAMENT for use in the treatment of inflammatory bowel disease in a subject. The MEDICAMENT of the present invention can be used in any of the methods of treatment described herein. The MEDICAMENT of the present invention is preferably used for the treatment and/or amelioration, or prevention of IBD, preferably an acute or relapsing phase of IBD. Preferred diseases which are to be treated, ameliorated or prevented in the context of the present invention (therapeutically or prophylactically) are selected from diseases, which can be subsumed under the collective term inflammatory bowel disease (IBD), ulcerative colitis and Crohn's disease being particularly preferred.

Generally, medical therapy for IBD has three main goals (1) Inducing remission (periods of time that are symptom-free); (2) Maintaining remission (preventing flare-ups of disease); (3) Improving the patient's quality of life.

To achieve these goals, therapy must suppress the chronic intestinal inflammation that causes the symptoms of IBD. When the inflammation is under control, the intestines can absorb essential nutrients. This, in turn, enables patients to avoid surgery and long-term complications.

Currently, there are five basic categories of medications used in the treatment of IBD: aminosalicylates, corticosteroids, immunomodulators, antibiotics, and biologic therapies. Some of the more common drugs used to treat IBD include sulfasalazine (Azulfadine), mesalamine (Asacol, Pentasa), azathioprine (Imuran), 6-MP (Purinethol), cyclosporine, methotrexate, infliximab (Remicade) and corticosteroids (prednisone).

Also, anti-TNFα antibodies are used in the treatment of IBD, such as infliximab, adalimumab, certolizumab pegol and golimumab. Upon a continuous application of such anti-TNFα antibodies, any immunosuppressive drug needs to be simultaneously applied.

Thus, the present invention further relates to a MEDICAMENT for use in the treatment of inflammatory bowel disease in a subject, wherein said subject is characterized by an increase of SEQ ID NO: 1 or 2 and by no alteration of S100A8 in comparison to a control subject or control value.

Equally, the present invention relates to a MEDICAMENT for use in the treatment of inflammatory bowel disease in a subject, wherein said subject is characterized by an increase of SEQ ID and by an increase of S100A8 in comparison to a control subject or control value. The present invention further relates to a MEDICAMENT for use in the treatment of inflammatory bowel disease in a subject, wherein said subject is characterized by an increase of SEQ ID NO: 1 or 2 in comparison to a control subject or control value.

In addition the present invention also envisages monitoring of disease progression. As such, the present invention further relates to the use of the level of SEQ ID NO: 1 or 2 in a test sample of a subject suffering from inflammatory bowel disease, for monitoring the progression of said disease in said subject. A "progression" of the disease is e.g. depicted in FIG. 1 of the present invention. It includes an acute phase and can also include further remissions and/or relapsing phases of IBD (see FIG. 1A). The severity of all these phases can be different from each other.

Moreover, "monitoring" means that any of the nucleic acid molecules of SEQ ID NO: 1 or 2 are periodically tested in a test sample of a patient or subject in clinical remission on medication or off medication or in a patient in stable remission on medication or off medication. Preferably, the patient is monitored with a periodicity of every month, every two months every three months, every six months, every year. For example a patient/subject in stable remission off medication can be monitored for a periodicity of one or two or three months for the year after the drug withdrawal. After one year, the periodicity can be changed to 6 months or one year.

The subject of the present invention can differ in its S100A8 level/expression when compared to a control subject. Therefore, in one embodiment, the subject has an unchanged expression of S100A8 mRNA or protein as compared to a control subject. In another embodiment, the subject has an unchanged or increased expression of S100A8 mRNA or protein as compared to a control subject. In one embodiment, the subject has an increased expression of S100A8 mRNA or protein as compared to a control subject. In another embodiment, the control subject is a healthy subject.

Thus, the present invention further relates to the use of a nucleic acid molecule selected of any of SEQ ID NO: 1 or 2 for in vitro diagnosis of an acute or relapsing phase of inflammatory bowel disease. Likewise, the present invention further relates to the use of a nucleic acid molecule selected of any of SEQ ID NO: 1 or 2 for in vitro diagnosis of a remission phase of inflammatory bowel disease.

As such, the present invention can also relate to the use of a nucleic acid molecule selected of any of SEQ ID NO: 1 or 2 for in vitro diagnosis of the absence of an acute or relapsing phase of inflammatory bowel disease. In some embodiments, the use of a nucleic acid molecule selected of any of SEQ ID NO: 1 or 2 is for in vitro diagnosis of the absence of an acute phase of inflammatory bowel disease. In other embodiments, the use of a nucleic acid molecule selected of any of SEQ ID NO: 1 or 2 is for in vitro diagnosis of the absence of a relapsing phase of inflammatory bowel disease.

The level of the nucleic acid molecules and/or the level of S100A8, S100A9 and/or calprotectin can be measured/detected by utilization of an adequate device. Therefore, the present invention further relates to a device for the diagnosis of an acute or relapsing phase of inflammatory bowel disease of a subject, wherein the device comprises oligonucleotide sequences to which any of SEQ ID NO: 1 or 2 hybridizes to detect the level of a nucleic acid molecule of SEQ ID NO: 1 or 2 in a test sample. Similarly, the present invention further relates to a device for the diagnosis of a remission phase or the absence of an acute or relapsing phase of inflammatory bowel disease of a subject, wherein the device comprises oligonucleotide sequences to which any of SEQ ID NO: 1 or 2 hybridizes to detect the level of a nucleic acid molecule of SEQ ID NO: 1 or 2 in a test sample.

The term "hybridizes" as used in accordance with the present invention may relate to hybridizations under stringent or non-stringent conditions. If not further specified, the conditions are preferably stringent. Said hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington DC, (1985). The setting of conditions is well known within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Notably variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed).

The terms "complementary" or "complementarity" refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands.

Also kits are envisioned by the present invention. Thus, the present invention further relates to a kit comprising one or more extraction buffer/reagents and protocol; reverse transcription buffer/reagents and protocol; and qPCR buffer/reagents and protocol suitable for performing any of the methods of the present invention. In one embodiment, the kit of the present invention is a kit-of-parts.

The kit or kit-of-parts of the present invention can comprise 1, 2, 3, 4, 5, 6, 7, 8, 9, 10, 11, 12, 20, 30, 40, 50 or more primers. Also envisaged are kits or kit-of-parts comprising primers specific for the nucleic acid molecule of SEQ ID NO: 1 or 2. Also envisaged are kits or kit-of-parts comprising primers specific for the nucleic acid molecule of SEQ ID NO: 1 or 2 and primers specific for S100A8 mRNA. In one embodiment, the kit or kit-of-parts of the present invention can further comprise nucleoside triphosphates. For example only dNTPs or rNTPs may be present kit or kit-of-parts of the present invention. It can also be that 1, 2 or 3 different types of dNTPs are present kit or kit-of-parts of the present invention. It can also be that 1, 2 or 3 different types of rNTPs are present kit or kit-of-parts of the present invention.

In one embodiment, the kit or kit-of-parts of the present invention further optionally comprises
  a) one or more buffer(s);
  b) reagents for quantifications, particularly reagents that bind to double stranded DNA particularly SYBR Green;
  c) one or more control values or control sequences or control samples; and/or
  d) one or more templates.

In one embodiment, the buffer comprised in the kit or kit-of-part comprises a buffer, in which the reverse transcription can take place. In another embodiment, the buffer comprised in the kit or kit-of-part comprises a buffer, suitable for the formation of primer/miRNA and/or primer/mRNA complexes. In further embodiments, the buffer comprised in the kit or kit-of-part comprises a buffer, suitable for the storage of the primers, control sequences and/or control samples.

The kit or kit-of-parts of the present invention can further optionally comprise reagents for quantifications. The reagent for quantification includes dyes that bind to double stranded DNA, as disclosed herein. In addition, the kit or kit-of-parts of the present invention further optionally comprises one or more control values or control sequences, such as the control values or control sequences as described herein. Also, the kit or kit-of-parts of the present invention further optionally comprises one or more templates, such as the test sample or control sample as described herein. It is also envisioned that the kit or kit-of-parts of the present invention further optionally comprises the nucleic acid molecule of the present invention. Additionally, the kit or kit-of-parts of the present invention further optionally comprises the vector of the present invention. The kit or kit-of-parts of the present invention further optionally comprises the host cell of the present invention.

The present invention also relates to the nucleic acid molecules of the present invention. Thus, the present invention further envisions nucleic acid molecules comprising the SEQ ID NO: 1 or 2, preferably SEQ ID NO: 1.

Similarly, the present invention also pertains to a vector or host cell comprising the nucleic acid molecule of the present invention. As such a "vector" as used herein refers to a recombinant DNA or RNA plasmid or virus that comprises a heterologous nucleic acid sequence capable of being delivered to a target cell, either in vitro, in vivo or ex-vivo. The nucleic acid sequence can be operably linked to another nucleic acid sequence such as promoter or enhancer and may control the transcription of the nucleic acid sequence of interest. As used herein, a vector need not be capable of replication in the ultimate target cell or subject. The term vector may include expression vector and cloning vector. An "expression vector" refers to a recombinant DNA or RNA construct, such as a plasmid, a phage, recombinant virus or other vector that, upon introduction into an appropriate host cell, results in expression of the inserted DNA. Appropriate expression vectors include those that are replicable in eukaryotic cells and/or prokaryotic cells and those that remain episomal or those which integrate into the host cell genome. The term "vector" or "expression vector" is used herein thus means nucleic acid based vectors which are used in accordance with the present invention as a vehicle for introducing into and expressing the nucleic acids molecules of the instant invention (in particular a nucleic acid molecule consisting of or comprising the sequence AAAAGCUGGGUUGAGAGGGCGA SEQ ID NO: 1 or AAAAGCUGGGUUGAGAGGGCGAA SEQ ID NO: 2) or complementary sequences thereof in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene, and the ability to enter and/or replicate in eukaryotic or prokaryotic cells. Additionally elements may also be included in the vector such as signal sequences, splice signals, as well as transcriptional promoters, enhancers, and termination signals. Examples of suitable vectors include, but are not limited to plasmids pcDNA3, pHCMV/Zeo, pCR3.1, pEF I/His, pEMD/GS, pRc/HCMV2, pSV40/Zeo2, pTRACER-HCMV, pUB6/V5-His, pVAXI, and pZeoSV2 (available from Invitrogen, San Diego, Calif.), and plasmid pCI (available from Promega, Madison, Wis.).

In a further embodiment, the present invention relates to a host cell comprising the nucleic acid molecule or complementary sequences thereof and/or the vector of the invention. The term "host cell" includes inter alia a bacterium (probiotic bacteria being preferred), preferably a gram-negative bacterium, more preferably a bacterium belonging to the family enterobacteriacea, and even more preferred a member of the genus *Escherichia*. In another preferred embodiment of the present invention, said host cell is a probiotic bacterium. Probiotic bacteria are, according to the definition set forth by the WHO bacteria associated with beneficial effects for humans and animals. The term "probiotic" further includes live, non-pathogenic microorganisms (preferably bacteria) which can confer a health benefit on the host, at least a health benefit for the gastrointestinal tract. Useful probiotics host cells include but are not limited to *Bacillus coagulans, Bifidobacterium animalis* subsp. *Lactis, Bifidobacterium breve, Bifidobacterium infantis, Bifidobacterium animalis, Bifidobacterium longum, Escherichia coli* M-17, *Escherichia coli* Nissle 1917, *Lactobacillus acidophilus, Lactobacillus casei, Lactobacillus paracasei, Lactobacillus fortis, Lactobacillus johnsonii, Lactococcus lactis, Lactobacillus plantarum, Lactobacillus Lactobacillus reuteri, Lactobacillus rhamnosus, Lactobacillus rhamnosus, Saccharomyces cerevisiae, especially boulardii, Lactobacillus rhamnosus, Streptococcus thermophilus, Lactobacillus helveticus*, mixtures thereof, and/or other bacteria of the above-listed genera.

In a particularly preferred embodiment, said probiotic host cell is selected from *E.coli* Nissle 1917 or *E. coli* 8178 DSM21844 (disclosed in WO2010/034479). The *Escherichia coli* strain Nissle 1917 is one of the best-studied probiotic strains. It is commercially available from ARDEYPHARM GmbH, Herdecke, Germany, under the trademark 'Mutaflor'. This particular *E. coli* strain was isolated in 1917 by Alfred Nissle based on its potential to protect from infectious gastroenteritis. The Nissle 1917 strain has been shown to combine efficient intestinal survival and colonization with the lack of virulence.

The present invention also relates to a pharmaceutical composition comprising an inhibitor of the nucleic acid molecule of the present invention, preferably a nucleic acid molecule of SEQ ID NO: 1.

"Inhibitors" of the present invention are any molecules that inhibit the nucleic acid moelules of the present invention e.g. inhibit their expression or function. Thus, inhibitors of the expression of the nucleic acid molecule of the present invention envisage also lentiviral vectors to knock down microRNA by overexpressing microRNA target sequences from polymerase II promoters (Gentner et al. (2009) Stable knockdown of microRNA in vivo by lentiviral vectors Nature Methods 6, 63-66), miRNA sponges (Ebert M S, Neilson J R, Sharp P A (2007) MicroRNA sponges: competitive inhibitors of small RNAs in mammalian cells. Nat Methods, 4:721-726; Ebert M S, Sharp P A (2010) MicroRNA sponges: progress and possibilities RNA, 16:2043-50), chemically modified antisense oligonucleotides, e.g. termed antimiRs (Stenvang et al. (2012) Inhibition of microRNA function by antimiR oligonucleotides. Silence 3:1), antisense nucleic acids (which are complementary sequences to the nucleic acid molcules of the present invention) as e.g. described in Cheng et al. (Cheng et al. (2005) Antisense inhibition of human miRNAs and indications for an involvement of miRNA in cell growth and apoptosis, Nucleic Acids Research, Volume 33, Issue 4, Pp. 1290-1297) or publicly available miRNA inhibitors such as miScript miRNA Inhibitors from Quiagen.

Also the inhibitors can be comprised by a vector or host cell.

The pharmaceutical composition of the present invention can comprise an inhibitor to a nucleic acid molecule of the present invention as an active ingredient and may further include a pharmaceutically acceptable carrier. A "pharmaceutically acceptable carrier" refers to an ingredient in a pharmaceutical formulation, other than an active ingredient, which is nontoxic to a subject. A pharmaceutically acceptable carrier includes, but is not limited to, a buffer (preferably an artificial buffer), excipient, stabilizer, and/or preservative. In regard to the treatment of colitis ulcerosa, it is particularly preferred that the pharmaceutical composition of the present invention comprises a buffer. In addition, the pharmaceutical composition of the invention may include other medicinal or pharmaceutical agents, adjuvants, etc. Exemplary parenteral administration forms include solutions or suspensions of active compound(s) in sterile aqueous solutions, for example, aqueous propylene glycol or dextrose solutions. Such dosage forms can be suitably buffered, if desired. Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof. Methods of preparing various pharmaceutical compositions with a specific amount of active compound are known, or will be apparent, to those skilled in this art. For examples—see Remington's Pharmaceutical Sciences, Mack Publishing Company, Ester, Pa., 15.sup.th Edition (1975). It will be understood, however, that the compositions of the invention may further comprise other components.

The (pharmaceutical) composition may, for example, be in a form suitable for oral administration as a tablet, capsule, pill, powder, sustained release formulations, solution, suspension, for parenteral injection as a sterile solution, suspension or emulsion or for rectal administration as a suppository. Oral administration is preferred, and as regards the treatment of colitis ulcerosa, oral administration is particularly preferred. The pharmaceutical composition may be in unit dosage forms suitable for single administration of precise dosages.

The nucleic acid molecules, vectors, host cells and/or compositions of the present invention may be used in a diagnostic and/or therapeutic medical setting.

It is also envisaged that the inhibitor of the nucleic acid molecules of the invention be provided in free form or bound to (for example covalently) and/or encompassed by a solid carrier, such as liposomes, nanotransporters, composites, metal complexes, polymers or biopolymers such as hydroxyapatite, nanoparticles, microparticles or any other vehicle considered useful for the delivery of nucleic acid molecules (including the vectors of the invention). Also envisoned are exosomes, which might be used as an in vivo protein or RNA carrier. The carrier e.g. the solid carrier comprising the inhibitor to the nucleic acid molecule of the present invention is preferably for use as a MEDICAMENT, and in particular for use in the treatment and/or amelioration, or prevention of a disease which disease is characterized by an elevation the nucleic acid molecule of the present invention in a test sample in comparison to a control sample or a control value.

A variety of compounds have been developed that complex with inhibitors as e.g. nucleic acids, to deliver them to surfaces of cells, and facilitate their uptake in and release from endosomes. Among these are: (1) a variety of lipids such as DOTAP (or other cationic lipid), DDAB, DHDEAB, and DOPE and (2) non-lipid-based polymers like polyethylenimine, polyamidoamine, and dendrimers of these and other polymers. In certain of these embodiments a combination of lipids is employed such as DOTAP and cholesterol or a cholesterol derivative (U.S. Pat. No. 6,770,291, which is hereby incorporated by reference). Several of these reagents have been shown to facilitate inhibitor uptake such as nucleic acid uptake in animals and all these compounds or compounds having a comparable mode of action (i.e. facilitate the uptake of nucleic acid molecules into cells, preferably into human cells) are encompassed by the embodiments of the present invention.

A variety of compounds have been attached to the ends of inhibitors such as nucleic acid molecules to facilitate their uptake/transport across cell membranes. Short signal peptides found in the HIV TAT, HSV VP22, *Drosphila antennapedia,* and other proteins have been found to enable the rapid transfer of biomolecules across membranes (reviewed by Schwarze 2000). These signal peptides, referred to as Protein Transduction Domains (PTDs), have been attached to oligonucleotides to facilitate their delivery into cultured cells. Cholesterols have been conjugated to oligonucleotides to improve their uptake into cells in animals (MacKellar 1992). The terminal cholesterol groups apparently interact with receptors or lipids on the surfaces of cells and facilitate the internalization of the modified oligonucleotides. Likewise, poly-1-lysine has been conjugated to oligonucleotides to decrease the net negative charge and improve uptake into cells (Leonetti 1990). All these entities which facilitate the uptake of nucleic acid molecules/vectors are also within the scope of the present invention.

In one embodiment, the inhibitors of the invention are supplied along with an ingestible support material for human consumption. Exemplary ingestible support materials include a cereal based food product, rice cake, soy cake, food bar product, cold formed food bar. The inhibitors discussed herein may be provided, for example, as dietary supplements, food and beverage additives, food and beverage ingredients.

It is also envisaged that the food or beverage products described herein above are intended for healthy subjects, preferably mammals and more preferably humans. Thus, the present invention also relates to the inhibitors for the supply of healthy subjects, and/or for promoting or conserving gut health or the wellbeing of a subject, preferably a human subject.

In a further embodiment, the present invention relates to a method of production of a food or beverage product, comprising the step of formulating the inhibitor of the nucleic acid molecule of the present invention or in admixture) into a food or beverage product.

Sequences

| | | | |
|---|---|---|---|
| SEQ ID NO. 1 | hsa-miR-320a mature sequence | aaaagcuggguugagagggcga (hsa = *Homo sapiens*) |
| SEQ ID NO. 1 | mmu-miR-320-3p mature sequence | aaaagcuggguugagagggcga (mmu = *Mus musculus*) |
| SEQ ID NO. 1 | bta-miR-320 mature sequence | aaaagcuggguugagagggcga (bta-*Bos taurus*) |
| SEQ ID NO. 1 | ppy-miR-320a mature sequence | aaaagcuggguugagagggcga (ppy = *Pongo pygmaeus*) |
| SEQ ID NO. 1 | ptr-miR-320a mature sequence | aaaagcuggguugagagggcga (ptr = *Pan troglodytes*) |
| SEQ ID NO. 1 | cfa-miR-320 mature sequence | Aaaagcuggguugagagggcga (cfa = *Canis familiaris*) |
| SEQ ID NO. 1 | rno-miR-320-3p mature sequence | Aaaagcuggguugagagggcga (rno = *Rattus norvegicus*) |
| SEQ ID NO. 1 | mml-miR-320 mature sequence | Aaaagcuggguugagagggcga (mml = *Macaca mulatta*) |
| SEQ ID NO. 1 | cgr-miR-320a mature sequence | aaaagcuggguugagagggcga (cgr = *Cricetulus griseus*) |
| SEQ ID NO. 1 | ggo-miR-320a mature sequence | aaaagcuggguugagagggcga (ggo = *Gorilla gorilla*) |
| SEQ ID NO. 2 | ssc-miR-320 mature sequence | Aaaagcuggguugagagggcgaa (ssc = *Sus scrofa*) |
| SEQ ID NO. 3 | Primer 1 S100A8_for | cttcccacacgtgtatcccta |
| SEQ ID NO. 4 | Primer 2 S100A8_rev | ccaaataaccaaaccagcaga |
| SEQ ID NO. 5 | Primer 1 miR320a_for | "forward primer" from "Hs_miR-320a_1 miScript Primer Assay" of Qiagen: AAAAGCUGGGUUGAGAGGGCGA |
| SEQ ID NO. 6 (unknown) | Primer 2 miR320a_rev | Der "reverse primer" is the "Universal primer" from Qiagen: The sequence of the miScript Universal Primer is proprietary.<br>The Universal primer is provided in the "miScript Primer Assays" of Qiagen, which is described under the following webpage on Jul. 10, 2014:<br>http://www.qiagen.com/products/catalog/assay-technologies/mirna/miscript-primer-assays. |

The present invention is further characterized by the following list of items:
1. An in vitro method for diagnosing an acute or relapsing phase of inflammatory bowel disease in a subject, the method comprising
   i) determining the level of a nucleic acid molecule comprising any one of SEQ ID NO: 1 or 2 in a test sample;
   ii) comparing the level of the nucleic acid molecule determined in the test sample with a control sample;
      wherein an elevation of said nucleic acid molecule in the test sample is indicative of an acute or relapsing phase of said inflammatory bowel disease.
2. The method of item 1, wherein the nucleic acid molecule has the SEQ ID NO: 1.
3. Any one of the preceding items, wherein said subject is a mammal, preferably a human being.
4. Any one of the preceding items, wherein the level of the S100A8 mRNA in said subject exhibits no alteration when compared to the control subject.
5. Any one of the preceding items, wherein said method further comprises the step of determining the S100A8 mRNA level in said test sample and optionally comparing it to the level in the control sample.
6. Any one of the preceding items, wherein said test sample and/or said control sample is any sample obtained not using endoscopy.
7. Any one of the preceding items, wherein said test sample and/or said control sample is selected from stool, urine, blood, salvia.
8. Any one of the preceding items, wherein said test sample and/or said control sample is a blood sample.
9. Any one of the preceding items, wherein the level of the nucleic acid molecule is determined by qRT-PCR.
10. The method of item 5, wherein the level of S100A8 mRNA is determined by qRT-PCR.
11. Any one of the preceding items, wherein said method comprises the steps of
    a) extracting RNA from the test sample;
    b) performing qRT-PCR with specific oligonucleotides suitable to detect said nucleic acid molecule.
12. Any one of the preceding items, wherein the level of the nucleic acid molecule is detected by a method comprising:
    a) extracting RNA from said test sample;
    b) treating the obtained RNA with a reverse transcription reaction mixture comprising specific oligonucleotides corresponding to the nucleic acid molecule as defined in item 1 or 2, dNTPs and a reverse transcriptase under conditions allowing transcription of the nucleic acid molecule into complementary DNA (cDNA);
    c) quantitative detection of cDNA transcripts of said nucleic acid molecule, where in steps b) and c) can be either performed in separate reactions or in one reaction.
13. The method of item 11 or 12, wherein the extracting step is omitted.
14. The method of item 11 or 12, wherein said specific oligonucleotides are selected from a group consisting of SEQ ID NO: 3 and/or SEQ ID NO: 4.
15. A method for diagnosing the acute or relapsing phase of inflammatory bowel disease comprising:
    (a) determining the level of SEQ ID NO: 1 or 2 in a test sample;
    (b) determining the level of S100A8 mRNA in said test sample; and
    (c) comparing both levels to a control sample or control value;
    wherein an increase of said SEQ ID and no alteration of said S100A8 in comparison to said control sample or control value indicates the acute or relapsing phase of inflammatory bowel disease.
16. A method for treating the acute or relapsing phase of inflammatory bowel disease in a subject comprising:
    (a) determining the level of any of SEQ ID NO: 1 or 2 in a test sample;
    (b) determining the level of S100A8 mRNA in said test sample;
    (c) comparing both levels to a control sample or control value; and
    (d) treating said subject with MEDICAMENT, provided that said test sample is characterized by an increase of said SEQ ID and by no alteration of said S100A8 in comparison to said control sample or control value.
17. MEDICAMENT for use in the treatment of inflammatory bowel disease in a subject, wherein said subject is characterized by an increase of SEQ ID NO: 1 or 2 and by no alteration of S100A8 in comparison to a control subject or control value.
18. Use of the level of SEQ ID NO: 1 or 2 in a test sample of a subject suffering from inflammatory bowel disease, for monitoring the progression of said disease in said subject.
19. Use of a nucleic acid molecule selected of any of SEQ ID NO: 1 or 2 for in vitro diagnosis of an acute or relapsing phase of inflammatory bowel disease.
20. Use of item 18 or 19, wherein the subject has an unchanged expression of S100A8 mRNA as compared to a control subject.
21. Use of item 20, wherein the control subject is a healthy subject.
22. A device for the diagnosis of an acute or relapsing phase of inflammatory bowel disease of a subject, wherein the device comprises oligonucleotide sequences to which any of SEQ ID NO: 1 or 2 hybridizes to detect the level of a nucleic acid molecule as defined in item 1 in a test sample.
23. A kit comprising one or more extraction buffer/reagents and protocol; reverse transcription buffer/reagents and protocol; and qPCR buffer/reagents and protocol suitable for performing the method of any one of the preceding items.
24. A method for diagnosing the acute phase of inflammatory bowel disease comprising:
    (a) determining the level of SEQ ID NO: 1 or 2 in a test sample;
    (b) determining the level of S100A8 mRNA in said test sample; and
    (c) comparing both levels to a control sample or control value;
    wherein an increase of said SEQ ID and no alteration or an increase of said S100A8 in comparison to said control sample or control value indicates the acute phase of inflammatory bowel disease.
25. A method for diagnosing an acute phase of inflammatory bowel disease comprising:
    (a) determining the level of SEQ ID NO: 1 or 2 in a test sample;
    (b) determining the level of S100A8 protein in said test sample; and
    (c) comparing both levels to a control sample or control value;
    wherein an increase of said SEQ ID and no alteration or an increase of said S100A8 in comparison to said control sample or control value indicates the acute phase of inflammatory bowel disease.

26. A method for diagnosing a relapsing phase of inflammatory bowel disease comprising:
   (a) determining the level of SEQ ID NO: 1 or 2 in a test sample;
   (b) determining the level of S100A8 mRNA in said test sample; and
   (c) comparing both levels to a control sample or control value;
   wherein an increase of said SEQ ID and no alteration or an increase of said S100A8 in comparison to said control sample or control value indicates the relapsing phase of inflammatory bowel disease.

27. A method for diagnosing a relapsing phase of inflammatory bowel disease comprising:
   (a) determining the level of SEQ ID NO: 1 or 2 in a test sample;
   (b) determining the level of S100A8 protein in said test sample; and
   (c) comparing both levels to a control sample or control value;
   wherein an increase of said SEQ ID and no alteration or an increase of said S100A8 in comparison to said control sample or control value indicates the relapsing phase of inflammatory bowel disease.

28. A method for diagnosing a remission phase or the absence of an acute or relapsing phase of inflammatory bowel disease comprising:
   (a) determining the level of SEQ ID NO: 1 or 2 in a test sample;
   (b) comparing the level to a control sample or control value;
   wherein no difference of said SEQ ID in comparison to said control sample or control value indicates the remission phase or the absence of an acute or relapsing phase of inflammatory bowel disease.

EXAMPLES

The following examples illustrate the invention. These examples should not be construed as to limit the scope of this invention. The examples are included for purposes of illustration and the present invention is limited only by the claims.

Example 1

In recent years the T cell-based murine models for IBD has been developed. (e.g. Ostanin et al., (2006) T cell-induced inflammation of the small and large intestine in immunodeficient mice Am J Physiol Gastrointest Liver Physiol. 290(1):G109-19) This transfer model images the T cell arm of IBD quite closely. This model is supposed to be a suitable model for chronic colitis, which is induced by a disturbance of T cell homeostasis. The transfer of naïve T cells in 'recombinase-activating gene-1-deficient—(RAG−/−)' mice induces a colitis as well as an inflammation of the small intestine which also makes this model relevant for studies on the pathogenesis of Crohn's Disease (CD). The transfer of CD4+CD45RBhigh T cells from healthy donor mice in RAG−/− mice induces a pan-colitis after 4-5 weeks. This is manifest by weight loss and continues to aggravate until after approximately 8 weeks the condition develops to a full-blown inflammation. Using this model especially the early onset as well as the aggravation of inflammation can be monitored (see FIG. 1A).

The drawback of the T cell transfer model is that it depends very much on environmental factors like the particular composition of the animal house microbiota where the reliability of the development of colitis is concerned.

Example 2

The more toxic DSS- (or TNBS-) colitis models (e.g. Perše M, Cerar A., (2012) Dextran sodium sulphate colitis mouse model: traps and tricks. J Biomed Biotechnol.2012: 718617) are more reliable and predictable in their pathogenicity and therefore used more frequently.

Experimental Colitis was induced in C57BL/6 WT mice by administration of 3% dextran sodium sulphate (DSS) in drinking water for 7 days. The course of disease was monitored by daily measurement of body weight. On day 7 mice were then sacrificed or given normal drinking water for 6 days. The colitis was directly assessed by mouse colonoscopy with assessing the murine endoscopic index of colitis severity (MEICS). Histological damage was determined according to the Dielemann Score. Expression of miR-320a was determined by qRT-PCR in murine mucosal samples of colonic segments as well as in murine peripheral blood.

On day 7, DSS-treated mice revealed a significant loss of body weight as compared to control mice (81%±2.3 vs. 103%±1.6; P=0,006) (FIG. 2A). The MEICS was significantly increased at day 7 (0.7±0.3 vs. 7.3±0.4; P<0,001) (FIG. 2B). Accordingly, the histological damage at day 7 was markedly increased as compared to controls (0.5±0.2 vs. 21.7±8.2; P=0,001) (FIG. 2C, D). At day 13, endoscopic signs of inflammation were markedly ameliorated (MEICS 0.5±0.5) with a reduced histological damage as compared to day 7 (14.5±2.8 vs. 21.7±8.2; P<0.05) (FIG. 2C, D).

Tissue samples were taken from different parts of the colon (proximal, medial and distal) as well as at different points in time during disease development: "A group": No DSS in the drinking water for the whole experiment, "B group": DSS application until day 7, development of severe colitis, "C group": DSS was removed from drinking water at day 7 and the animals were able to recovery from the disease until day 14 (see also FIG. 2A: weight curve) (FIG. 4A).

In accordance with the massive histological damage, mucosal expression of miR-320a in the distal colon of colitic mice was significantly increased as compared to healthy controls (0.51±0.08 vs. 0.38±0.01; P=0.04). Furthermore, miR-320a expression in the whole colonic tissue correlated strongly with the severity of histological damage (r 2=0.73; P<0.05) (FIG. 3A, B).

The expression of the miRNA320a and S100A8 (calprotectin) in blood samples was analyzed in a defined time-frame (FIG. 4 D, E). Tested were the following groups: "A group": No DSS in the drinking water for the whole experiment, "B group": DSS application until day 4, "B group": DSS application until day 8, development of severe colitis, "D group": 15 days recovery. It becomes clear that the elevation of the expression of miRNA in the blood starts earlier (group B) than the elevation of the expression of S100A8.

The expression of the "inflammation marker" S100A8 (calprotectin) correlates with the time course of miRNA-320 expression in the accordant tissue samples (FIG. 4C) and the miR-320a expression in the blood correlated strongly with the severity of histological damage (FIG. 3C).

Changes in m- and mi-RNA expression were determined by Quantitative RT-PCR (qRT-PCR) employing the Light-Cycler system (Roche) and quantified using the 'Light Cycler software' Version 3 (Roche, Mannheim, Germany). Necessary primer pairs were designed using the Universal Probe Library Assay Design Center (Roche, Mannheim, Germany), synthesized by Eurofins MWG Operon (Ebersberg, Germany) or purchased as validated pairs from Qiagen (Hilden, Germany). The miR-320a expression strongly correlates between expression in tissue and blood samples (FIG. 4B).

In addition to the histological scoring the technique of 'confocal laser endoscopy (CLE)' in mice (Becker et al., (2006) High resolution colonoscopy in live mice. Nat Protoc. 1(6):2900-4) has been applied to demonstrate the time course of colitis development and recovery after withdrawal of DSS from the drinking water after day 7. The Coloview miniendoscopic system (Karl Storz, Tuttlingen, Germany) has been employed for these experiments. This technique presents a reliable, fast and high-quality technique for endoscopic characterization and molecular imaging of colitis in mice (Waldner et al., (2011) Confocal laser endomicroscopy and narrow-band imaging-aided endoscopy for in vivo imaging of colitis and colon cancer in mice. Nat Protoc. 6(9):1471-81). As it is necessary to follow histological changes for the characterization of intestinal pathologies over time, by employing this procedure, it is possible to evaluate each animal not only at one time point. Mouse endoscopy enables the early detection of mucosal inflammation and allows the characterization of disease progression during a certain experimental protocol in the same animal (Waldner et al., 2011 [more detailed information on the cited paper]), which increases the reliability of data and thereby reduce the number of animals needed in the study.

Generally, NBI endoscopy can be used as a 'red-flag' technology with any mouse model that leads to colonic diseases such as inflammation (e.g., chemical-induced models of colitis, such as dextran sulfate sodium (DSS)-induced or 2,4,6-trinitrobenzenesulfonic acid (TNBS)-induced colitis) or tumor development (e.g., azoxymethane (AOM)+DSS colitis, APCmin mice). NBI endoscopy is especially helpful for the detection of small dysplastic lesions that might have been missed by conventional endoscopy, as NBI endoscopy improves the detection of aberrant vessel formations.

Example 3

MiRNA levels in human blood from Crohns disease patients with acute flare and healthy controls were determined (n=5 per group).

In human blood from Crohn's disease patients with an acute flare, miR-320a expression was significantly increased as compared to healthy controls (0.25±0.17 vs. 1.9±1.15; P=0.03) FIG. 3D).

MicroRNA Expression analysis from stool and serum samples from human patients during Crohn's Disease (CD) and Ulcerative Colitis (CD). RNA was isolated from 100 µl samples according to Qiagens "Animal blood Kit" instructions and reverse transcribed into cDNA according to "miScript II RT Kit" using the "HighFlex" buffer system (Qiagen, Hilden). For FIG. 5A: Pairs of samples represent in each case the same patient in relapse and remission (Rem) phase dating back to 1997 revealing the stability of miRNAs in body fluids (FIG. 5A+B).

MiRNA expression in actual total blood samples (2012) from patients in remission (rem) and flare (FIG. 5C).

Example 4

'Infectious disease' model based on the application attenuated *Salmonella thyphimurium* to C57/BL/6J mice. In this model chronic inflammation in the gut of C57/BL/6J mice is induced by infection with an attenuated ΔaroA mutant of *Salmonella enterica* serovar *Typhimurium* or a LPS mutant (ΔmsbB) which do not cause a lethal inflammation of the gut (Stecher et al., (2005) Comparison of *Salmonella enterica* serovar *Typhimurium* colitis in germ-free mice and mice pretreated with streptomycin. Infect Immun. 2005 June; 73(6):3228-41; Hapfelmeier et al., (2005) The *Salmonella* pathogenicity island (SPI)-2 and SPI-1 type III secretion systems allow *Salmonella* serovar *typhimurium* to trigger colitis via MyD88-dependent and MyD88-independent mechanisms. J Immunol. 174(3):1675-85; Nell et al., (2010) The impact of the microbiota on the pathogenesis of IBD: lessons from mouse infection models. Nat Rev Microbiol. 8(8):564-77; Grassi et al., (2010) CD34 mediates intestinal inflammation in *Salmonella*-infected mice. Cell Microbiol. 12(11):1562-75). The course of the disease is self-limited in this case: after seven days after infection the cecum, as the most effected part of the gut during this inflammation, reveals the first signs of disease accompanied by a light fibrosis, after 14 to 21 days a full blown colitis is achieved but due to the attenuated *Salmonella* strain the disease is cured again in the following week. (FIG. 6A+B).

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein. Unless otherwise indicated, the term "at least" preceding a series of elements is to be understood to refer to every element in the series. At least one includes for example, one, two, three, four, or five or even more.

Those skilled in the art will recognize, or be able to ascertain using no more than routine experimentation, many equivalents to the specific embodiments of the invention described herein. Such equivalents are intended to be encompassed by the present invention. Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Provided that the present specification refers to a defined nucleic acid sequence, said sequence is depicted in its 5' to 3'orientation (unless otherwise specified in the text).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

The invention claimed is:

1. An in vitro method for diagnosing an acute or relapsing phase of inflammatory bowel disease in a subject, the method comprising
   i) determining the level of a nucleic acid molecule comprising the nucleotide sequence of SEQ ID NO: 1 or 2 in a test sample of stool, urine, blood, or saliva;
   ii) comparing the level of the nucleic acid molecule determined in the test sample with a control sample; wherein an elevation of said nucleic acid molecule in the test sample is indicative of an acute or relapsing phase of said inflammatory bowel disease; and
   iii) treating the subject diagnosed with the acute or relapsing phase of inflammatory bowel disease with a medicament.

2. The method of claim 1, wherein the nucleic acid molecule comprises the nucleotide sequence of SEQ ID NO: 1.

3. The method of claim 2, wherein the level of S100A8 mRNA in said subject exhibits no alteration when compared to a control subject.

4. The method of claim 2, wherein said method further comprises the step of determining the S100A8 mRNA level in said test sample and optionally comparing it to the level in the control sample.

5. The method of claim 1, wherein said subject is a mammal.

6. The method of claim 5, wherein said mammal is a human.

7. The method of claim 1, wherein the level of S100A8 mRNA in said subject exhibits no alteration when compared to a control subject.

8. The method of claim 1, wherein said method further comprises the step of determining the S100A8 mRNA level in said test sample and optionally comparing it to the level in the control sample.

9. The method of claim 8, wherein the level of S100A8 mRNA is determined by qRT-PCR.

10. The method of claim 1, wherein said control sample is any sample obtained not using endoscopy.

11. The method of claim 1, wherein said control sample is stool, urine, blood, or saliva.

12. The method of claim 1, wherein said test sample and/or said control sample is a blood sample.

13. The method of claim 1, wherein the level of the nucleic acid molecule is determined by qRT-PCR.

14. The method of claim 1, wherein said method comprises the steps of
   a) optionally extracting RNA from the test sample; and
   b) performing qRT-PCR with specific oligonucleotides suitable to detect said nucleic acid molecule.

15. The method of claim 1, wherein the level of the nucleic acid molecule is detected by a method comprising:
   a) optionally extracting RNA from said test sample;
   b) treating the RNA from the test sample with a reverse transcription reaction mixture comprising specific oligonucleotides corresponding to the nucleic acid molecule comprising the nucleotide sequence of SEQ ID NO: 1 or 2, deoxynucleotide triphosphates (dNTPs) and a reverse transcriptase under conditions allowing transcription of the nucleic acid molecule into complementary DNA (cDNA); and
   c) detecting quantitatively cDNA transcripts of said nucleic acid molecule,
   wherein steps b) and c) can be either performed in separate reactions or in one reaction.

16. A method for treating an acute or relapsing phase of inflammatory bowel disease in a subject comprising:
   (a) determining the level of the nucleotide sequence of SEQ ID NO: 1 or 2 in a test sample of stool, urine, blood, or saliva;
   (b) determining the level of S1008A mRNA in said test sample;
   (c) comparing both levels to a control sample or control value; and
   (d) treating said subject with a medicament, provided that said test sample is characterized by an increase of said level of the nucleotide sequence of SEQ ID NO: 1 or 2 and by no alteration of said level of the S1008A mRNA in comparison to said control sample or control value.

* * * * *